United States Patent
Matsuyama et al.

(10) Patent No.: US 9,512,362 B2
(45) Date of Patent: Dec. 6, 2016

(54) COMPOUND, LIQUID CRYSTAL COMPOSITION, POLYMER MATERIAL AND FILM

(71) Applicant: FUJIFILM Corporation, Tokyo (JP)

(72) Inventors: Hiroshi Matsuyama, Ashigarakami-gun (JP); Shunya Katoh, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 71 days.

(21) Appl. No.: 14/478,913

(22) Filed: Sep. 5, 2014

(65) Prior Publication Data

US 2014/0374657 A1 Dec. 25, 2014

Related U.S. Application Data

(63) Continuation of application No. PCT/JP2013/055720, filed on Mar. 1, 2013.

(30) Foreign Application Priority Data

Mar. 7, 2012 (JP) ................. 2012-050097

(51) Int. Cl.

| | |
|---|---|
| *C09K 19/22* | (2006.01) |
| *C09K 19/54* | (2006.01) |
| *C09K 19/56* | (2006.01) |
| *C09K 19/40* | (2006.01) |
| *C07C 235/48* | (2006.01) |
| *C07C 235/50* | (2006.01) |
| *C09K 19/20* | (2006.01) |
| *C09K 19/28* | (2006.01) |
| *C09K 19/36* | (2006.01) |
| *C09K 19/32* | (2006.01) |
| *C09K 19/34* | (2006.01) |
| *C09K 19/04* | (2006.01) |

(52) U.S. Cl.
CPC ............. *C09K 19/56* (2013.01); *C07C 235/48* (2013.01); *C07C 235/50* (2013.01); *C09K 19/2007* (2013.01); *C09K 19/2014* (2013.01); *C09K 19/22* (2013.01); *C09K 19/28* (2013.01); *C09K 19/32* (2013.01); *C09K 19/3488* (2013.01); *C09K 19/3491* (2013.01); *C09K 19/36* (2013.01); *C09K 19/40* (2013.01); *C09K 2019/044* (2013.01); *C09K 2019/0429* (2013.01); *C09K 2019/0448* (2013.01); *C09K 2019/2078* (2013.01); *C09K 2019/3408* (2013.01)

(58) Field of Classification Search
CPC ... C07C 235/48; C07C 235/50; C07C 69/76; C09K 19/22; C09K 19/2007; C09K 19/34; C09K 19/36; C09K 19/40; C09K 19/56; C09K 2019/0429; C09K 2019/0444; C09K 2019/0448; C09K 2019/2014
See application file for complete search history.

(56) References Cited

U.S. PATENT DOCUMENTS 6,875,483 B2    4/2005  Ichihashi et al.
2002/0039627 A1  4/2002  Ichihashi et al.

FOREIGN PATENT DOCUMENTS

JP    2002-129162 A    5/2002

OTHER PUBLICATIONS

Cheng et al, "Molecular Design of Liquid-Crystalline Block Molecules: Semifluorinated Pentaerythritol Tetrabenzoates Exhibiting Lamellar, Columnar, and Cubic Mesophases", Angew. Chem. Int. Ed. 2000, 39, No. 3, pp. 592-595.*
International Search Report, issued in PCT/JP2013/055720, dated Jun. 4, 2013.
Written Opinion of the International Searching Authority, issued in PCT/JP2013/055720, dated Jun. 4, 2013.
International Preliminary Report on Patentability dated Sep. 18, 2014, issued in PCT/JP2013/055720 (Forms PCT/IB/338, PCT/IB/373, PCT/ISA/237 and PCT/IB/326).

* cited by examiner

*Primary Examiner* — Shean C Wu
(74) *Attorney, Agent, or Firm* — Birch, Stewart, Kolasch & Birch, LLP

(57) ABSTRACT

A liquid crystal composition comprising a compound represented by the following formula has sufficient solubility and a wide usable concentration range, and exhibits excellent haze-lowering performance. $B^1$ represents an n-valent chain linking group, $L^1$ and $L^2$ represent a single bond, —O—, —S—, —CO—, —COO—, —OCO—, etc, $A^1$ represents a divalent aromatic hydrocarbon group or a divalent heterocyclic group, $A^2$ represents an aromatic hydrocarbon group, $Sp^1$ represents a single bond, or an alkylene group, $Hb^1$ represents a fluorine-substituted alkyl group, n represents 2 to 6, m represents 0 to 2, and l represents 2 or 3.

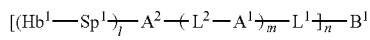

16 Claims, 1 Drawing Sheet

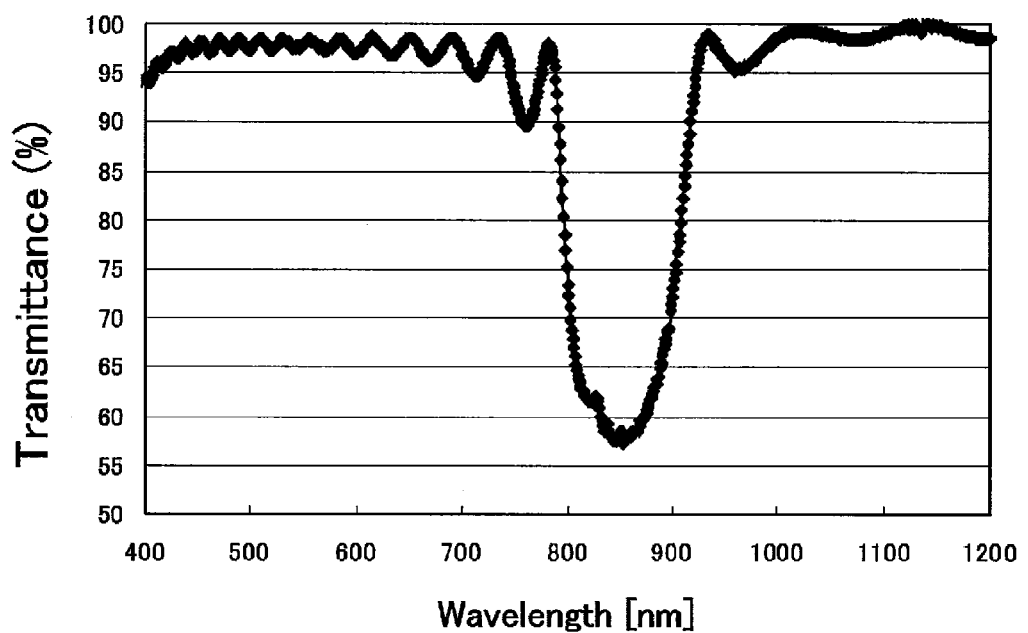

COMPOUND, LIQUID CRYSTAL COMPOSITION, POLYMER MATERIAL AND FILM

CROSS-REFERENCE TO RELATED APPLICATIONS

This application is a Continuation of PCT International Application No. PCT/JP2013/055720 filed Mar. 1, 2013, which claims priority under 35 U.S.C. Section 119(a) to Japanese Patent Application No. 2012-050097 filed Mar. 7, 2012. Each of the above applications is hereby expressly incorporated by reference, in its entirety, into the present application.

BACKGROUND OF THE INVENTION

Field of the Invention

The present invention relates to compounds useful in a variety of applications, including materials of various types of optical members such as optically anisotropic films and heat shield films, and to liquid crystal compositions and polymer materials containing such compounds. The invention also relates to films that use such materials.

Background Art

Liquid crystals orderly align themselves upon being applied onto a film subjected to an alignment process (alignment film). The alignment state of liquid crystal can be controlled with the use of two alignment films disposed on the both sides of the liquid crystal. An example of such a structure is a liquid crystal display device that includes a liquid crystal cell constructed from rod-like liquid crystal molecules and a pair of substrates sealing the liquid crystal molecules, and an electrode layer provided to apply voltage to the rod-like liquid crystal molecules. In such a liquid crystal display device, the rod-like liquid crystal molecules are injected into the gap between the alignment films formed on the two substrates, and the alignment state of the rod-like liquid crystal molecules can be controlled relatively easily.

On the other hand, it has been proposed to dispose an optical compensation sheet (retardation plate) between a liquid crystal cell and a polarizing plate for the purpose of increasing the viewing angle or preventing coloring of a liquid crystal display device. In this case, an optically anisotropic element having an optically anisotropic layer formed from liquid crystal molecules is used as an optical compensation sheet on a transparent support. The optically anisotropic layer is formed by aligning liquid crystal molecules, and fixing the alignment state. Here, the liquid crystal molecules are aligned with a single alignment film provided between the transparent support and the optically anisotropic layer. However, it is difficult with a single alignment film to uniformly align (monodomain alignment) the liquid crystal molecules from the alignment film interface to the air interface. This is because of the disturbed liquid crystal alignment due to the lack of alignment regulation on the side of the interface (air interface) not subjected to an alignment process. Non-uniform alignment of liquid crystal molecules causes scattering of light due to disclination, and a nontransparent film is formed. Such a film is not desirable from the standpoint of improving the viewability of the liquid crystal display device.

Out of these needs, a technique is developed that regulates alignment of a liquid crystal and uniformly aligns the liquid crystal also on the side of the interface (air interface) not subjected to an alignment process, without using an alignment film (Patent Reference 1). In this technique, alignment of the liquid crystal molecules is controlled by adding a liquid crystal alignment promoting agent that has a discotic core and terminal long-chain fluorinated alkyl. By using the liquid crystal alignment promoting agent, a liquid crystal composition is provided that allows liquid crystal molecules to uniformly align themselves with ease.

CITATION LIST

Patent Reference

Patent Reference 1: JP-A-2002-129162

SUMMARY OF INVENTION

However, the liquid crystal alignment promoting agent described in Patent Reference 1 is not necessarily sufficient in terms of usable concentration range and solubility, and needs further improvements. There is accordingly a need for a compound that has a liquid crystal alignment promoting effect at least comparable to that of the liquid crystal alignment promoting agent described in Patent Reference 1, and that can lower the haze of the product film. It is accordingly an object of the present invention to solve the foregoing problems of related art, and provide a compound that has sufficient solubility and a wide usable concentration range, and that exhibits excellent haze-lowering performance upon being added to a liquid crystal composition to produce a film. Another object is to provide a novel liquid crystal composition that can lower the haze of the product film by allowing liquid crystal molecules to uniformly align themselves with ease or the like. Specifically, the present invention is intended to provide a compound useful for a variety of applications, including materials of various types of optical members such as optically anisotropic films and heat shield films. The invention is also intended to provide a liquid crystal composition and a polymer material containing such a compound, and a film that uses such materials.

The present inventors conducted intensive studies to solve the foregoing problems, and found that compounds having a chain linking group as a core linking moiety are highly capable of stabilizing liquid crystal alignment. After further studies, it was found that a compound obtained by appropriately introducing a fluorinated alkyl-containing side chain to a molecule of a specific structure having a chain linking group in the core can lower the haze of a film produced with a liquid crystal composition containing such a compound. The present invention has been completed on the basis of these findings.

The foregoing problems are solved by the following means.

[1] A liquid crystal composition comprising a compound represented by the following formula (1), and a liquid crystal molecule:

Formula (1)

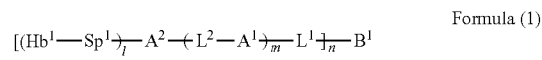

In the formula (1), $B^1$ represents an n-valent chain linking group of 1 to 40 carbon atoms wherein the chain linking group contains at least one $—CR^{101}R^{102}—$, and $R^{101}$ and $R^{102}$ each independently represent a hydrogen atom, a halogen atom, $—COOH$, $—SO_3H$, $—SH$, $—NH_3$, or $—OH$, and not containing a cyclic structure, $L^1$ and $L^2$ each independently represent a single bond, —O—, —S—, —CO—, —COO—, —OCO—, —COS—, —SCO—, —C(=S)O—, —NR⁰CO—, or —CONR⁰— wherein $R^0$ represents a hydrogen atom or an alkyl group of 1 to 6 carbon atoms, $A^1$ represents a divalent aromatic hydrocarbon group or a divalent heterocyclic group, $A^2$ represents an (l+1)-valent aromatic hydrocarbon group, $Sp^1$ represents a single bond, or an alkylene group of 1 to 10 carbon atoms wherein a methylene group in the alkylene group may be substituted with —O—, —S—, —CO—, —COO—, —OCO—, —COS—, —SCO—, —NR¹CO—, or —CONR¹— in which $R^1$ represents a hydrogen atom, or an alkyl group of 1 to 6 carbon atoms, provided that any two consecutive methylene groups are not both substituted, and wherein a hydrogen atom of the alkylene may be substituted with a halogen atom or a hydroxyl group, $Hb^1$ represents a fluorine-substituted alkyl group of 4 to 30 carbon atoms, n represents an integer of 2 to 6, m represents an integer of 0 to 2, l represents 2 or 3, and $L^1$, $L^2$, $A^1$, $A^2$, $Sp^1$, $Hb^1$, m, and l occurring more than once in formula (1) may be the same or different.

[2] It is preferable in the liquid crystal composition of [1] that $B^1$ in the formula (1) contain at least one unsubstituted methylene group.

[3] It is preferable in the liquid crystal composition of [1] or [2] that, in the formula (1), n is 2, $B^1$ represents an alkylene group of 1 to 40 carbon atoms, wherein a methylene group in the alkylene group may be substituted with —O—, —S—, —CO—, —COO—, —OCO—, —COS—, —SCO—, —NR²CO—, —CONR²—, —NR²CONR²—, —NR²—, —CR²=CR²—, —C≡C—, or —CR²R²— in which $R^2$ each independently represents a hydrogen atom, or an alkyl group of 1 to 10 carbon atoms, and a hydrogen atom in the alkylene group may be substituted with a halogen atom, —COOH, —SO₃H, —SH, —NH₃, or —OH, provided that any two consecutive methylene groups are not both substituted and $B^1$ does not contain a cyclic structure.

[4] It is preferable in the liquid crystal composition of [1] or [2] that, in the formula (1), n is 2, $B^1$ represents alkylene of 1 to 40 carbon atoms, wherein a methylene group in the alkylene group may be substituted with —O—, —S—, —CO—, —COO—, —OCO—, —COS—, —SCO—, —NR⁵CO—, —CONR⁵—, or —NR⁵CONR⁵— in which $R^5$ each independently represents a hydrogen atom, or an alkyl group of 1 to 6 carbon atoms, and a hydrogen atom in the alkylene may be substituted with a halogen atom, provided that any two consecutive methylene groups are not both substituted, and $B^1$ does not contain a cyclic structure.

[5] It is preferable in the liquid crystal composition of [1] or [2] that, in the formula (1), n is 2, $B^1$ represents alkylene of 1 to 40 carbon atoms, wherein a methylene group in the alkylene group may be substituted with —O—, —S—, —NR⁶—, or —NR⁶CONR⁶— in which $R^6$ each independently represents a hydrogen atom, or an alkyl group of 1 to 6 carbon atoms, and a hydrogen atoms in the alkylene group may be substituted with a halogen atom, provided that any two consecutive methylene groups are not both substituted.

[6] It is preferable in the liquid crystal composition of any one of [1] to [5] that the compound represented by the formula (1) be a compound represented by the following formula (2):

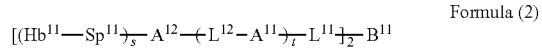

Formula (2)

In the formula (2), $B^{11}$ represents alkylene of 1 to 40 carbon atoms wherein a methylene group in the alkylene may be substituted with —O—, —S—, —CO—, —COO—, —OCO—, —COS—, —SCO—, —NR¹²CO—, —CONR¹²—, —NR¹²CONR¹²—, —NR¹²—, —CR¹²=CR¹²—, —C≡C—, or —CR¹²R¹²— in which $R^{12}$ each independently represents a hydrogen atom, or an alkyl group of 1 to 10 carbon atoms, provided that any two consecutive methylene groups are not both substituted, and wherein a hydrogen atom in the alkylene group may be substituted with a halogen atom, provided that that the alkylene group contains at least one unsubstituted methylene group, and wherein $B^{11}$ does not contain a cyclic structure, $L^{11}$ represents —COO—, —COS—, or —CONR¹⁰—, $L^{12}$ represents a single bond, —O—, —S—, —CO—, —COO—, —OCO—, —COS—, —SCO—, —NR¹⁰CO—, or —CONR¹⁰— in which $R^{10}$ each independently represents a hydrogen atom, or an alkyl group of 1 to 6 carbon atoms, $A^{11}$ represents a divalent aromatic hydrocarbon group or a divalent heterocyclic group, $A^{12}$ represents an (s+1)-valent aromatic hydrocarbon group, $Sp^{11}$ represents a single bond, or an alkylene group of 1 to 10 carbon atoms wherein a methylene group in the alkylene group may be substituted with —O—, —S—, —CO—, —COO—, —OCO—, —COS—, —SCO—, —NR¹¹CO—, or —CONR¹¹— in which $R^{11}$ represents a hydrogen atom, or an alkyl group of 1 to 6 carbon atoms, and a hydrogen atom in the alkylene group may be substituted with a halogen atom, $Hb^{11}$ represents a fluorine-substituted alkyl group of 4 to 30 carbon atoms, s represents an integer of 0 to 2, t represents 2 or 3, and $L^{11}$, $L^{12}$, $A^{11}$, $A^{12}$, $Sp^{11}$, $Hb^{11}$, s and t occurring more than once in formula (2) each independently may be the same or different.

[7] It is preferable in the liquid crystal composition of [6] that s in the formula (2) be 3.

[8] It is preferable in the liquid crystal composition of [6] or [7] that, in the formula (2), t represents 0 or 1, and $L^{11}$ and $L^{12}$ both be —COO—.

[9] It is preferable in the liquid crystal composition of any one of [1] to [8] that the liquid crystal molecule be a polymerizable rod-like liquid crystal molecule.

[10] It is preferable that the liquid crystal composition of any one of [1] to [9] contain at least one chiral compound.

[11] A polymer material as a polymerized material of the liquid crystal composition of any one of [1] to [10].

[12] A film that contains at least one polymer material of [11].

[13] A film with a fixed cholesteric liquid crystal phase of the liquid crystal composition of any one of [1] to [10].

[14] It is preferable that the film of [12] or [13] have optical anisotropy.

[15] It is preferable that the film of any one of [12] to [14] have a selective reflection characteristic.

[16] It is preferable that the film of [15] have a selective reflection characteristic in an infrared wavelength region.

[17] A compound represented by the following formula (2): Formula (2)

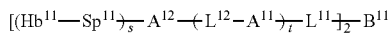

In the formula (2), $B^{11}$ represents an alkylene group of 1 to 40 carbon atoms, a methylene group in the alkylene group may be substituted with —O—, —S—, —CO—, —COO—, —OCO—, —COS—, —SCO—, —NR$^{12}$CO—, —CONR$^{12}$—, —NR$^{12}$CONR$^{12}$—, —NR$^{12}$—, —CR$^{12}$=CR$^{12}$—, —C≡C—, or —CR$^{12}$R$^{12}$ in which R$^{12}$ each independently represents a hydrogen atom, or an alkyl group of 1 to 10 carbon atoms, provided that any two consecutive methylene groups are not both substituted, and a hydrogen atom in the alkylene group may be substituted with a halogen atom, provided that the alkylene contains at least one unsubstituted methylene group, and wherein B$^{11}$ does not contain a cyclic structure, $L^{11}$ represents —COO—, —COS—, or —CONR$^{10}$—, and $L^{12}$ represents a single bond, —O—, —S—, —CO—, —COO—, —OCO—, —COS—, —SCO—, —NR$^{10}$CO—, or —CONR$^{10}$— in which R$^{10}$ each independently represents a hydrogen atom, or an alkyl group of 1 to 6 carbon atoms, $A^{11}$ represents a divalent aromatic hydrocarbon group or a divalent heterocyclic group, $A^{12}$ represents an (s+1)-valent aromatic hydrocarbon group, $Sp^{11}$ represents a single bond, or an alkylene group of 1 to 10 carbon atoms, a methylene group in the alkylene group may be substituted with —O—, —S—, —CO—, —COO—, —OCO—, —COS—, —SCO—, —NR$^{11}$CO—, or —CONR$^{11}$— in which R$^{11}$ represents a hydrogen atom, or an alkyl group of 1 to 6 carbon atoms, provided that any two consecutive methylene groups are not both substituted, and wherein a hydrogen atoms in the alkylene maybe substituted with a halogen atom, $Hb^{11}$ represents a fluorine-substituted alkyl group of 4 to 30 carbon atoms, s represents an integer of 0 to 2, t represents 2 or 3, and $L^{11}$, $L^{12}$, $A^{11}$, $A^{12}$, $Sp^{11}$, $Hb^{11}$, s and t occurring more than once in formula (2) each independently may be the same or different.

[18] It is preferable in the compound of [17] that s in the formula (2) be 3.

[19] It is preferable in the compound of [17] or [18] that, in the formula (2), t represents 0 or 1, and $L^{11}$ and $L^{12}$ both be —COO—.

The present invention uses an alignment promoting agent of formula (1) having a wide usable concentration range, high solvent solubility, and a high liquid crystal alignment promoting effect, and can provide a liquid crystal composition and a polymer material useful for a variety of applications, including materials of various types of optical members such as optically anisotropic films and heat shield films. The invention also can provide a film that uses such materials.

BRIEF DESCRIPTION OF DRAWINGS

FIG. 1 represents a transmission spectrum of the film of Example 11.

DESCRIPTION OF EMBODIMENTS

The present invention is described below in detail.

The descriptions of the constituting elements below, including the representative embodiments and concrete examples thereof according to the present invention, serve solely to illustrate the present invention, and the present invention is not limited by such embodiments and concrete examples. As used herein, the numerical ranges defined with "to" are intended to be inclusive of the numbers specified by "to" as the lower limit and the upper limit.

[Liquid Crystal Composition]

A liquid crystal composition of the present invention includes a compound represented by the following formula (1), and a liquid crystal molecule:

Formula (1)

In the formula (1), $B^1$ represents an n-valent chain linking group of 1 to 40 carbon atoms {the chain linking group contains at least one —CR$^{101}$R$^{102}$— (R$^{101}$ and R$^{102}$ each independently represent a hydrogen atom, a halogen atom, —COOH, —SO$_3$H, —SH, —NH$_3$, or —OH), and not containing a cyclic structure}, $L^1$ and $L^2$ each independently represent a single bond, —O—, —S—, —CO—, —COO—, —OCO—, —COS—, —SCO—, —C(=S)O—, —NR$^0$CO—, or —CONR$^0$— (wherein R$^0$ represents a hydrogen atom or an alkyl group of 1 to 6 carbon atoms), $A^1$ represents a divalent aromatic hydrocarbon group or a divalent heterocyclic group, $A^2$ represents an (l+1)-valent aromatic hydrocarbon group, $Sp^1$ represents a single bond, or an alkylene group of 1 to 10 carbon atoms {wherein a methylene group in the alkylene group may be substituted with —O—, —S—, —CO—, —COO—, —OCO—, —COS—, —SCO—, —NR$^1$CO—, or —CONR$^1$— (wherein R$^1$ represents a hydrogen atom, or an alkyl group of 1 to 6 carbon atoms), and wherein a hydrogen atom in the alkylene may be substituted with a halogen atom or hydroxyl, provided that any two consecutive methylene groups are not both substituted}, $Hb^1$ represents a fluorine-substituted alkyl group of 4 to 30 carbon atoms, n represents an integer of 2 to 6, m represents an integer of 0 to 2, l represents 2 or 3, and $L^1$, $L^2$, $A^1$, $A^2$, $Sp^1$, $Hb^1$, m, and l occurring more than once in formula (1) may be the same or different.

With such a configuration, the liquid crystal composition of the present invention can lower the haze of the product film. Without being bound to any theory, a molecule with a chain linking group contained as a core linking moiety has a high degree of freedom, and a compound having such a backbone has a flexible structure, and can align liquid crystal molecules even under high concentrations. Such compounds thus have a wide latitude for the alignment stability of liquid crystal molecules, and are highly capable of stabilizing alignment. With two or more fluorinated alkyl groups at the both ends of the molecule, the compound represented by formula (1) has an improved surface distribution, and can promote alignment of liquid crystal molecules.

As used herein, "liquid crystal alignment promoting agent" means a compound that reduces haze when the liquid crystal composition is aligned and cured with the compound more than when the liquid crystal composition is aligned and cured without the compound. The liquid crystal alignment promoting agent is also referred to as haze lowering agent or haze reducing agent. The compound represented by the formula (1) below may preferably be added as a liquid crystal alignment promoting agent (a haze-lowering agent, or a haze reducing agent) to the liquid crystal composition.

The following describes the preferred structures of the compounds of formula (1) used for the liquid crystal composition of the present invention, along with the synthesis methods of the compounds of formula (1), and preferred compositions for the liquid crystal composition of the present invention.

<Compounds of Formula (1)>

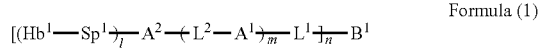

Formula (1)

In formula (1), $B^1$ represents an n-valent chain linking group of 1 to 40 carbon atoms {the chain linking group contains at least one $-CR^{101}R^{102}-$ ($R^{101}$ and $R^{102}$ each independently represent a hydrogen atom, a halogen atom, $-COOH$, $-SO_3H$, $-SH$, $-NH_3$, or $-OH$), and not containing a cyclic structure}.

Here, the chain linking group not containing a cyclic structure means that the chain linking group does not contain cyclic structures such as an aromatic ring, an aliphatic ring, and a heterocyclic ring, and the chain linking group may be branched or linear.

In the compounds represented by formula (1), $B^1$ representing a chain linking group has such a structure, and is contained as a core linking moiety to provide the effects of the present invention.

$R^{101}$ and $R^{102}$ each independently represent a hydrogen atom, a halogen atom, $-COOH$, $-SO_3H$, $-SH$, or $-OH$, more preferably a hydrogen atom or a halogen atom, particularly preferably a hydrogen atom or a fluorine atom, even more preferably a hydrogen atom. Specifically, it is preferable in the liquid crystal composition of the present invention that $B^1$ in the formula (1) contains at least one unsubstituted methylene group.

The n-valent chain linking group of 1 to 40 carbon atoms represented by $B^1$ contains at least one, preferably two or more, more preferably 2 to 20, particularly preferably 2 to 10 $-CR^{101}R^{102}-$.

The n-valent chain linking group of 1 to 40 carbon atoms represented by $B^1$ may contain a linking group other than $-CR^{101}R^{102}-$.

Such linking groups other than $-CR^{101}R^{102}-$ are not particularly limited, and are preferably $-O-$, $-S-$, $-CO-$, $-COO-$, $-OCO-$, $-COS-$, $-SCO-$, $-NR^2CO-$, $-CONR^2-$, $-NR^2CONR^2-$, $-NR^2-$, $-CR^2=CR^2-$, $-C\equiv C-$, or $-CR^2R^2-$ ($R^2$ each independently represent a hydrogen atom, or an alkyl group of 1 to 10 carbon atoms), more preferably $-O-$, $-S-$, $-CO-$, $-COO-$, $-OCO-$, $-COS-$, $-SCO-$, $-NR^5CO-$, $-CONR^5-$, or $-NR^5CONR^5-$ ($R^5$ each independently represent a hydrogen atom, or an alkyl group of 1 to 6 carbon atoms), particularly preferably $-O-$, $-S-$, $-NR^6-$, or $-NR^6CONR^6-$ ($R^6$ each independently represent a hydrogen atom, or an alkyl group of 1 to 6 carbon atoms).

$R^2$ represents preferably a hydrogen atom, or an alkyl group of 1 to 6 carbon atoms, more preferably a hydrogen atom, or an alkyl group of 1 to 3 carbon atoms, particularly preferably a hydrogen atom or a methyl group, even more preferably a hydrogen atom. The alkyl represented by $R^2$ may be linear or branched.

$R^5$ and $R^6$ each independently represent preferably a hydrogen atom, or an alkyl group of 1 to 3 carbon atoms, more preferably a hydrogen atom or a methyl group, particularly preferably a hydrogen atom. The alkyl represented by $R^5$ and $R^6$ may be linear or branched.

The n-valent chain linking group of 1 to 40 carbon atoms represented by $B^1$ contains preferably 0 to 20, more preferably 0 to 10, particularly preferably 0 to 5 linking groups other than $-CR^{101}R^{102}-$.

In formula (1), n represents an integer of 2 to 6, preferably 2 to 4, more preferably 2 or 3, particularly preferably 2.

When n in formula (1) is 3 to 6, $B^1$ has at least one trivalent to hexavalent linking group. Examples of the trivalent to hexavalent linking group include $RC(-*)_3$, $*-RC=C(-*)_2$, $C(-*)_4$, and $N(-*)_3$, wherein R is a hydrogen atom or any substituent, and $-*$ is a bond (* represents any binding site, and is joined to $L^1$ either directly or via any other linking group). Preferred as the trivalent to hexavalent linking group are $RC(-*)_3$, and $C(-*)_4$.

The trivalent to hexavalent linking group is not cyclic, and is treated as a part of the chain linking group in this specification.

When n in formula (1) is 2, $B^1$ represents a divalent chain linking group of 1 to 40 carbon atoms.

Here, $B^1$ preferably represents an alkylene group of 1 to 40 carbon atoms, wherein a methylene group in the alkylene may preferably be substituted with $-O-$, $-S-$, $-CO-$, $-COO-$, $-OCO-$, $-COS-$, $-SCO-$, $-NR^2CO-$, $-CONR^2-$, $-NR^2CONR^2-$, $-NR^2-$, $-CR^2=CR^2-$, $-C\equiv C-$, or $-CR^2R^2-$ ($R^2$ each independently represents a hydrogen atom, or an alkyl group of 1 to 10 carbon atoms), provided that any two consecutive methylene groups are not both substituted and wherein a hydrogen atom in the alkylene group may preferably be substituted with a halogen atom, $-COOH$, $-SO_3H$, $-SH$, $-NH_3$, or $-OH$.

When $B^1$ represents an alkylene group of 1 to 40 carbon atoms, a hydrogen atom in the alkylene may be substituted with a halogen atom, $-COOH$, $-SO_3H$, $-SH$, $-NH_3$, or $-OH$, provided that $B^1$ contains at least one $-CR^{101}R^{102}-$ ($R^{101}$ and $R^{102}$ each independently represent a hydrogen atom, a halogen atom, $-COOH$, $-SO_3H$, $-SH$, $-NH_3$, or $-OH$).

In formula (1), $L^1$ and $L^2$ each independently represent a single bond, $-O-$, $-S-$, $-CO-$, $-COO-$, $-OCO-$, $-COS-$, $-SCO-$, $-C(=S)O-$, $-NR^0CO-$, or $-CONR^0-$ (wherein $R^0$ represents a hydrogen atom or an alkyl group of 1 to 6 carbon atoms), more preferably a single bond, $-O-$, $-S-$, $-CO-$, $-COO-$, $-OCO-$, $-COS-$, $-SCO-$, $-NR^{10}CO-$, or $-CONR^{10}-$ ($R^{10}$ each independently represents a hydrogen atom, or an alkyl group of 1 to 6 carbon atoms).

It is particularly preferable that $L^1$ represents $-O-$, $-COO-$, $-COS-$, or $-CONR^{10}-$, further preferably $-O-$ or $-COO-$, even more preferably $-COO-$.

It is particularly preferable that $L^2$ represents a single bond, $-O-$, $-COO-$, or $-OCO-$, further preferably $-O-$ or $-COO-$, even more preferably $-COO-$.

Preferred as the combination of $L^1$ and $L^2$ is a combination in which $L^1$ is —O— and $L^2$ is —O—, or $L^1$ is —COO— and $L^2$ is —COO—, more preferably a combination in which $L^1$ is —COO— and $L^2$ is —COO—.

Preferably, $R^0$ and $R^{10}$ each independently represent a hydrogen atom, or an alkyl group of 1 to 3 carbon atoms, more preferably a hydrogen atom or a methyl group, particularly preferably a hydrogen atom. The alkyl represented by $R^5$ and $R^6$ may be linear or branched.

In formula (1), $A^1$ represents a divalent aromatic hydrocarbon group or a divalent heterocyclic group, more preferably a divalent aromatic hydrocarbon group. The divalent aromatic hydrocarbon group is of preferably 6 to 22 carbon atoms, more preferably 6 to 14 carbon atoms, further preferably 6 to 10 carbon atoms, even more preferably 6 carbon atoms. When the divalent aromatic hydrocarbon group is of 6 carbon atoms, the divalent aromatic hydrocarbon group has bonds preferably at meta- or para-position, particularly preferably para-position. The divalent heterocyclic group has preferably a five-, six-, or seven-membered heterocyclic ring, more preferably a five- or six-membered ring, most preferably a six-membered ring. The heteroatom forming the heterocyclic ring is preferably a nitrogen atom, an oxygen atom, or a sulfur atom. The heterocyclic ring is preferably an aromatic heterocyclic ring. The aromatic heterocyclic ring is typically an unsaturated heterocyclic ring, preferably an unsaturated heterocyclic ring having the maximum number of double bonds. Examples of the heterocyclic ring include a furan ring, a thiophene ring, a pyrrole ring, a pyrroline ring, a pyrrolidine ring, an oxazole ring, an isooxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazan ring, a tetrazole ring, a pyran ring, a thiin ring, a pyridine ring, a piperidine ring, an oxazine ring, a morpholine ring, a thiazine ring, a pyridazine ring, a pyrimidine ring, a pyrazine ring, a piperazine ring, and a triazine ring.

The divalent aromatic hydrocarbon group or the divalent heterocyclic group represented by $A^1$ may have optional substituents. Examples of such substituents include an alkyl group of 1 to 8 carbon atoms, an alkoxy group, a halogen atom, and a group having a cyano group or an ester structure. The alkyl group as the substituent of the divalent aromatic hydrocarbon group or the divalent heterocyclic group represented by $A^1$ is of 1 to 8 carbon atoms, preferably 1 to 5 carbon atoms, more preferably 1 to 3 carbon atoms. The alkyl group may be linear, branched, or cyclic, and is preferably linear or branched. Preferred examples of the alkyl group include a methyl group, an ethyl group, a n-propyl group, and an isopropyl group.

The descriptions and the preferred range of the substituent alkyl group for the divalent aromatic hydrocarbon group or the divalent heterocyclic group represented by $A^1$ should be referred to for the alkyl moieties of the substituent alkoxy of the divalent aromatic hydrocarbon group or the divalent heterocyclic group represented by $A^1$.

Examples of the substituent halogen atoms of the divalent aromatic hydrocarbon group or the divalent heterocyclic group represented by $A^1$ include a fluorine atom, a chlorine atom, a bromine atom, and an iodine atom. Preferred are a chlorine atom, and a bromine atom.

Examples of the ester structure-containing substituent of the divalent aromatic hydrocarbon group or the divalent heterocyclic group represented by $A^1$ include groups represented by R'COO—. Examples of R' include an alkyl group of 1 to 8 carbon atoms. The descriptions and the preferred range of the substituent alkyl group for the divalent aromatic hydrocarbon group or the divalent heterocyclic group represented by $A^1$ should be referred to for explanations and the preferred range of the alkyl group represented by R'. Specific examples of the ester group include $CH_3COO$—, and $C_2H_5COO$—.

Preferred examples of the substituents for the divalent aromatic hydrocarbon group or the divalent heterocyclic group include a methyl group, an ethyl group, a methoxy group, an ethoxy group, a bromine atom, a chlorine atom, and a cyano group.

In formula (1), $A^2$ represents an (l+1)-valent aromatic hydrocarbon. The (l+1)-valent aromatic hydrocarbon is of preferably 6 to 22 carbon atoms, more preferably 6 to 14 carbon atoms, further preferably 6 to 10 carbon atoms, even more preferably 6 carbon atoms. When the (l+1)-valent aromatic hydrocarbon is of 6 carbon atoms, the (l+1)-valent aromatic hydrocarbon has bonds preferably at meta- or para-position, more preferably at least at para-position, particularly preferably at meta- and para-positions.

The (l+1)-valent aromatic hydrocarbon represented by $A^2$ may have optional substituents. Examples of such substituents include an alkyl group of 1 to 8 carbon atoms, an alkoxy group of 1 to 8 carbon atoms, a halogen atom, and a group containing a cyano group or an ester structure. The corresponding descriptions of the substituents for the divalent aromatic hydrocarbon group or the divalent heterocyclic group represented by $A^1$ should be referred to for explanations and the preferred range of these groups. Examples of the substituents for the (l+1)-valent aromatic hydrocarbon group represented by $A^2$ include a methyl group, an ethyl group, a methoxy group, an ethoxy group, a bromine atom, a chlorine atom, and a cyano group.

In formula (1), $Sp^1$ represents a single bond, or an alkylene group of 1 to 10 carbon atoms {wherein a methylene group in the alkylene may be substituted with a divalent linking group such as —O—, —S—, —CO—, —COO—, —OCO—, —COS—, —SCO—, —$NR^1CO$—, —$CONR^1$— (wherein $R^1$ represents a hydrogen atom, or an alkyl group of 1 to 6 carbon atoms), provided that any two consecutive methylene groups are not both substituted, and wherein a hydrogen atom in the alkylene group may be substituted with a halogen atom or a hydroxyl group}, more preferably a single bond, or an alkylene group of 1 to 7 carbon atoms, further preferably a single bond, or an alkylene group of 1 to 5 carbon atoms. The alkylene group may be branched or unbranched, and is preferably unbranched linear alkylene.

$R^1$ represents preferably a hydrogen atom, or alkyl of 1 to 3 carbon atoms, more preferably a hydrogen atom or methyl, particularly preferably a hydrogen atom. The alkyl represented by $R^1$ may be linear or branched.

When a methylene group in the alkylene group of 1 to 10 carbon atoms represented by $Sp^1$ is substituted, such methylene group is preferably substituted with —O—, —COO—, or —OCO—.

When a methylene group in the alkylene group of 1 to 10 carbon atoms represented by $Sp^1$ is substituted, the number of substituted methylene group is preferably 0 to 2, more preferably 0 or 1, particularly preferably 1.

When a hydrogen atom of the alkylene of 1 to 10 carbon atoms represented by $Sp^1$ are substituted, the hydrogen atom is preferably substituted with a halogen atom (particularly, a fluorine atom). It is, however, preferable in the compounds represented by the formula (1) that the hydrogen atoms of the alkylene group of 1 to 10 carbon atoms represented by $Sp^1$ are unsubstituted.

In formula (1), $Hb^1$ represents a fluorinated alkyl group of 2 to 30 carbon atoms, more preferably a fluorinated alkyl group of 4 to 30 carbon atoms, particularly preferably a fluorinated alkyl group of 4 to 10 carbon atoms. The fluorinated alkyl group may be or may not be substituted with a hydrogen atom. The fluorinated alkyl group may be linear, branched, or cyclic, and is preferably linear or branched, more preferably linear. For example, the fluorinated alkyl group is preferably one with a terminal perfluoroalkyl group, specifically a group represented by the following formula.

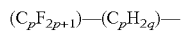

In this formula, p is preferably 1 to 30, more preferably 1 to 20, further preferably 1 to 10. q is preferably 0 to 20, more preferably 0 to 10, further preferably 0 to 5. p+q is preferably 3 to 30.

The fluorinated alkyl group used in the present invention may be one with a terminal $H-(C_pF_{2p})-(C_pH_{2q})-$ group, instead of a terminal perfluoroalkyl group.

When more than one $Hb^1$ exists, the plurality of $Hb^1$ may have the same or different structures. Preferably, the structures of the plurality of $Hb^1$ are the same.

In formula (1), m represents an integer of 0 to 2, preferably 0 or 1, more preferably 0.

In formula (1), l is 2 or 3, preferably 3.

$L^1$, $L^2$, $A^1$, $A^2$, $Sp^1$, $Hb^1$, m, and l occurring more than once in formula (1) may be the same or different. When l and m represent 2 or more, the structures in the parentheses with the subscripts l and m may be the same or different.

The compound represented by formula (1) maybe one having a symmetric molecular structure, or may be a compound with no symmetry. As used herein, "symmetry" is intended to mean point symmetry, line symmetry, or rotational symmetry, and "asymmetry" means anything that is not classified into point symmetry, line symmetry, or rotational symmetry.

Preferably, the terminal $Hb^1$-$Sp^1$- groups in the molecule of the compound represented by formula (1) are each independently a group represented by any of the following formulae.

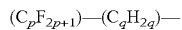

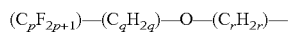

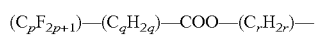

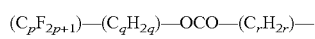

In the formulae, p is preferably 1 to 30, more preferably 1 to 20, further preferably 1 to 10. q is preferably 0 to 20, more preferably 0 to 10, further preferably 0 to 5. p+q is preferably 3 to 30. r is preferably 1 to 10, more preferably 1 to 4.

Preferably, the compounds represented by formula (1) are novel compounds represented by the formula (2) below, also from the standpoint of the advantageous effects of the present invention.

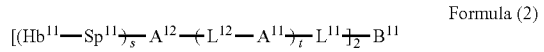

Formula (2)

In formula (2), $B^{11}$ represents an alkylene group of 1 to 40 carbon atoms {wherein a methylene group in the alkylene group may be substituted with —O—, —S—, —CO—, —COO—, —OCO—, —COS—, —SCO—, —NR$^{12}$CO—, —CONR$^{12}$—, —NR$^{12}$CONR$^{12}$—, —NR$^{12}$—, —CR$^{12}$=CR$^{12}$—, —C≡C—, or —CR$^{12}$R$^{12}$— ($R^{12}$ each independently represents a hydrogen atom, or an alkyl group of 1 to 10 carbon atoms), provided that any two consecutive methylene groups are not both substituted, and a hydrogen atom in the alkylene may be substituted with a halogen atom, provided that the alkylene group contains at least one unsubstituted methylene group}, $L^{11}$ represents —COO—, —COS—, or —CONR$^{10}$—, and $L^{12}$ represents a single bond, —O—, —S—, —CO—, —COO—, —OCO—, —COS—, —SCO—, —NR$^{10}$CO—, or —CONR$^{10}$— ($R^{10}$ each independently represents a hydrogen atom, or an alkyl group of 1 to 6 carbon atoms), $A^{11}$ represents a divalent aromatic hydrocarbon group or a divalent heterocyclic group, $A^{12}$ represents an (s+1)-valent aromatic hydrocarbon group, $Sp^{11}$ represents a single bond, or an alkylene group of 1 to 10 carbon atoms {wherein a methylene group in the alkylene group may be substituted with —O—, —S—, —CO—, —COO—, —OCO—, —COS—, —SCO—, —NR$^{11}$CO—, or —CONR$^{11}$— ($R^{11}$ represents a hydrogen atom, or an alkyl group of 1 to 6 carbon atoms), and wherein a hydrogen atom in the alkylene group may be substituted with a halogen atom}, $Hb^{11}$ represents a fluorine-substituted alkyl group of 4 to 30 carbon atoms, s represents an integer of 0 to 2, t represents 2 or 3, and $L^{11}$, $L^{12}$, $A^{11}$, $A^{12}$, $Sp^{11}$, $Hb^{11}$, s and t occurring more than once in formula (2) each independently may be the same or different.

The preferred range of $B^{11}$ in formula (2) is the same as the preferred range of $B^1$ of the formula (1).

$L^{11}$ in formula (2) represents —COO—, —COS—, or —CONR$^{10}$—, preferably —COO—.

$L^{12}$ in formula (2) represents a single bond, —O—, —S—, —CO—, —COO—, —OCO—, —COS—, —SCO—, —NR$^{10}$CO—, or —CONR$^{10}$— ($R^{10}$ each independently represents a hydrogen atom, or an alkyl group of 1 to 6 carbon atoms). The preferred range of $L^{12}$ is the same as the preferred range of $L^2$ in the formula (1).

Preferred as the combination of $L^{11}$ and $L^{12}$ in formula (2) is a combination in which $L^{11}$ is —COO— and $L^{12}$ is —COO—.

The preferred range of $A^{11}$ in formula (2) is the same as the preferred range of $A^1$ in the formula (1).

The preferred range of $A^{12}$ in formula (2) is the same as the preferred range of $A^2$ in the formula (1).

The preferred range of $Sp^{11}$ in formula (2) is the same as the preferred range of $Sp^1$ in the formula (1).

The preferred range of $Hb^{11}$ in formula (2) is the same as the preferred range of $Hb^1$ in the formula (1).

In formula (2), t represents an integer of 0 to 2, preferably 0 or 1, more preferably 0.

In formula (2), s is 2 or 3, preferably 3.

$L^{11}$, $L^{12}$, $A^{11}$, $A^{12}$, $Sp^{11}$, $Hb^{11}$, s and t occurring more than once in formula (2) each independently may be the same or different. When s and t represent 2 or more, the structures in the parentheses with the subscripts s and t may be the same or different.

Specific examples of the compounds represented by formula (1) are given below. It should be noted, however, that the compounds of formula (1) usable in the present invention should not be narrowly interpreted within the limits of the following specific examples.

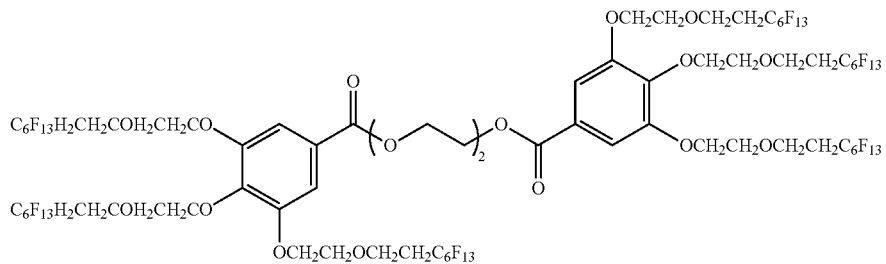
(1)
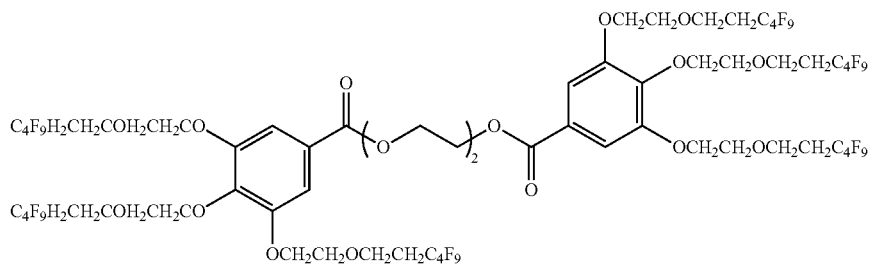
(2)
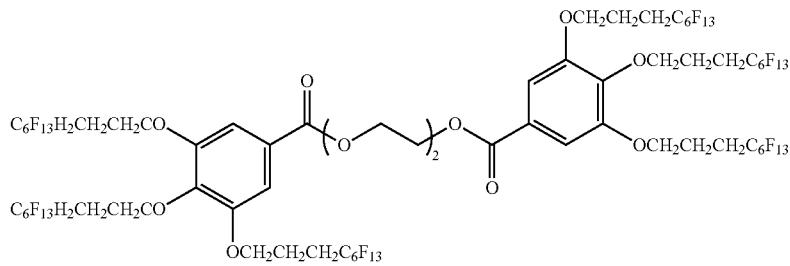
(3)
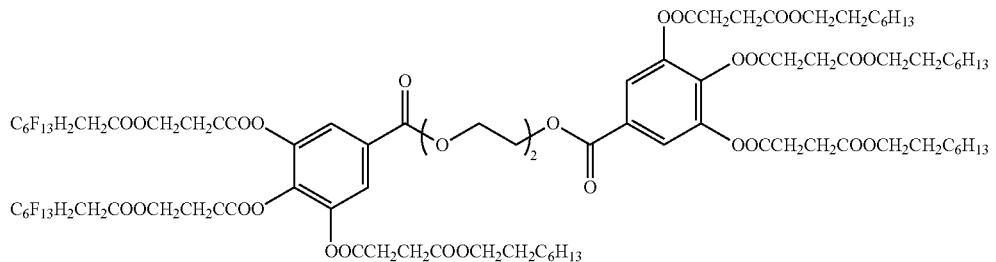
(4)
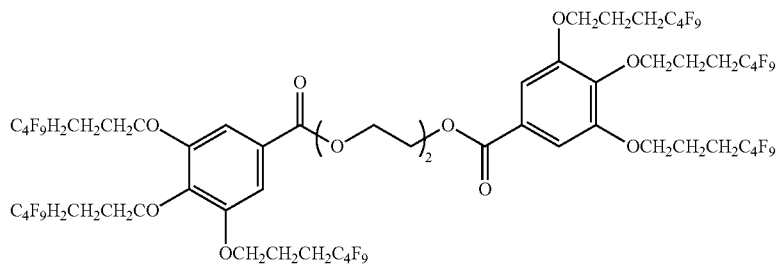
(5)
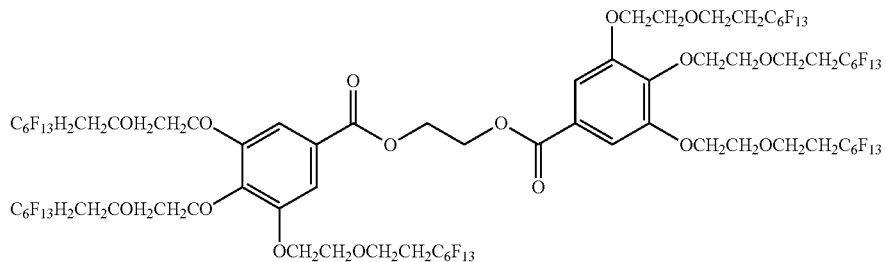
(6)

-continued
(7)
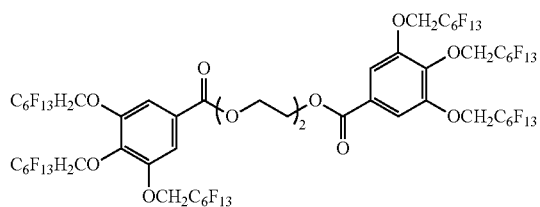
(8)
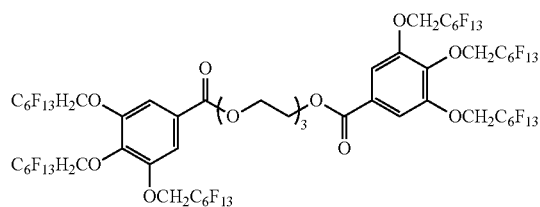
(9)
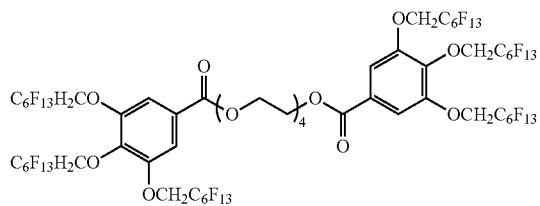
(10)
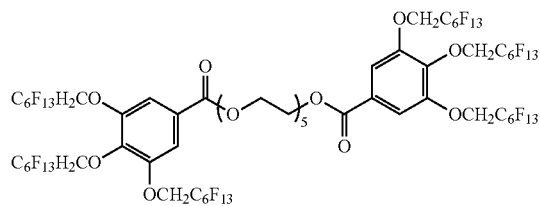
(11)
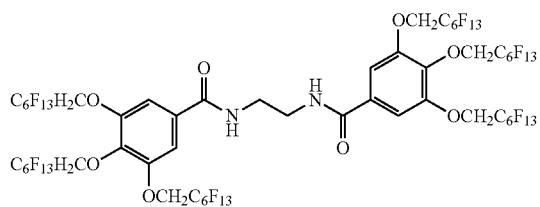
(12)
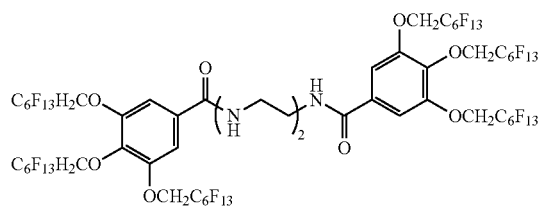
(13)
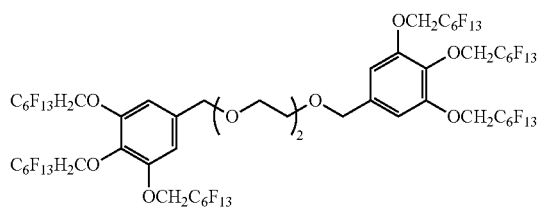
(14)
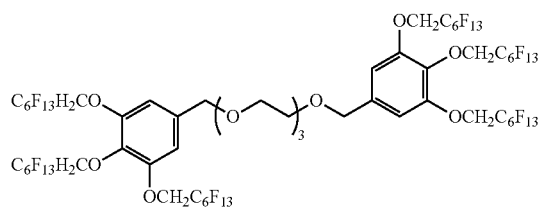
(15)
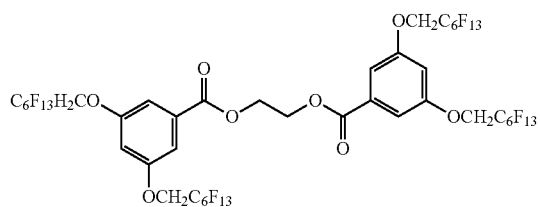
(16)
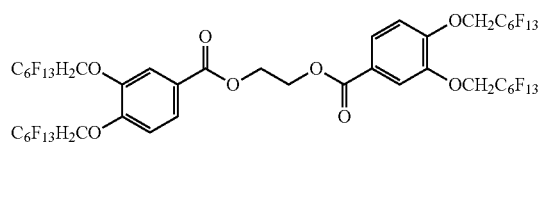
(17)
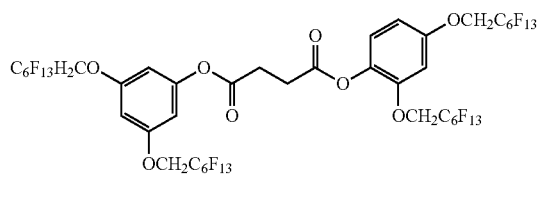
(18)
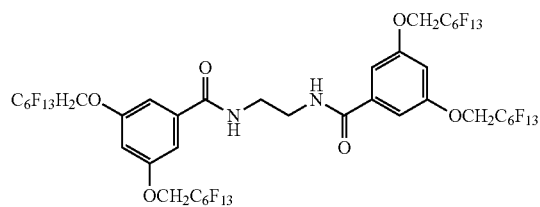
(19)
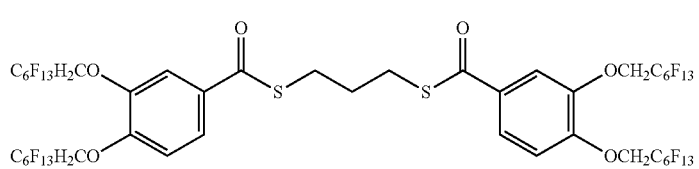

-continued
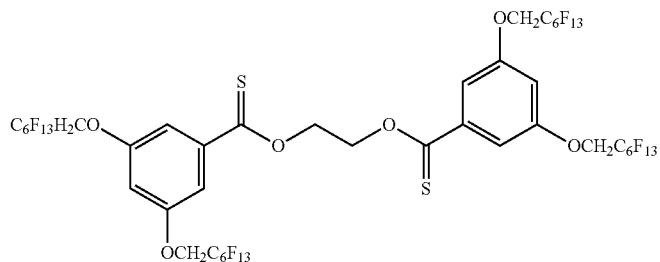
(20)
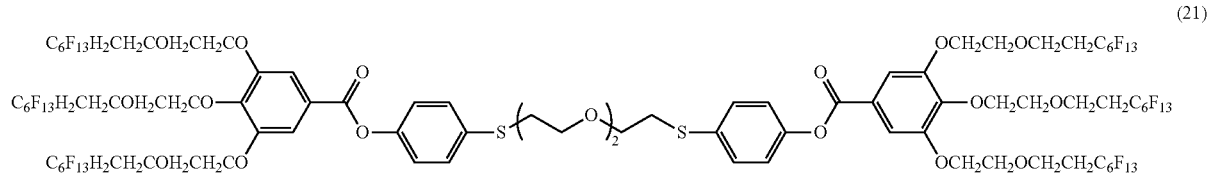
(21)
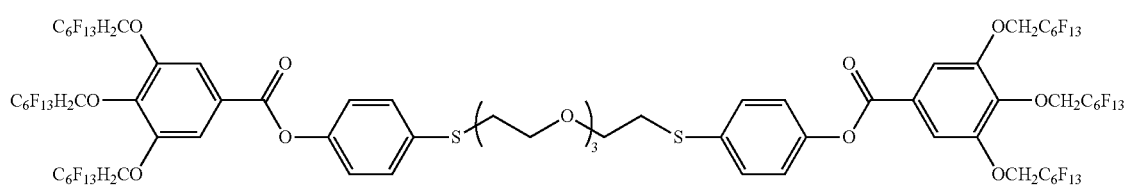
(22)
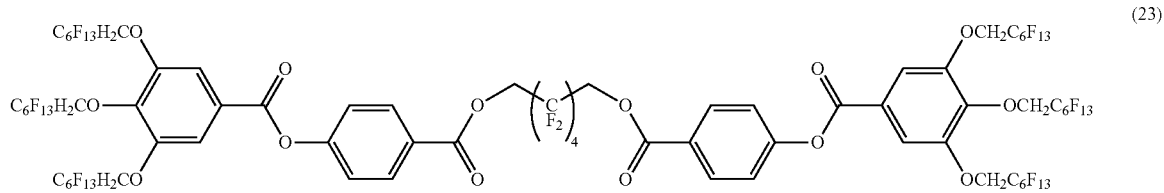
(23)
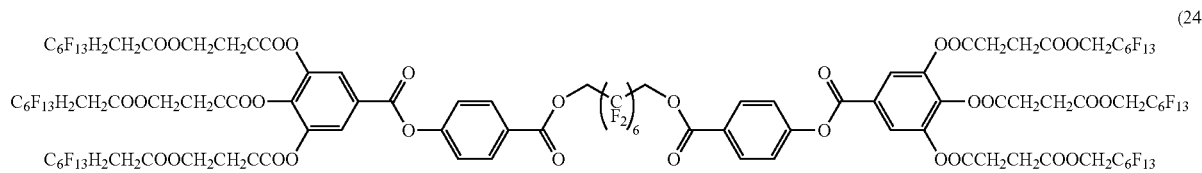
(24)
(25)
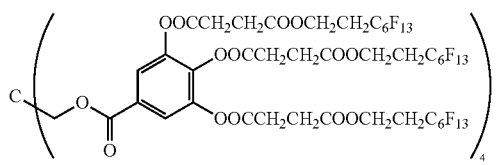
(26)
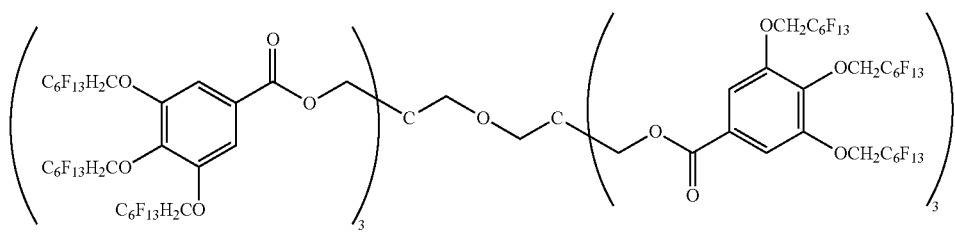
(27)

-continued
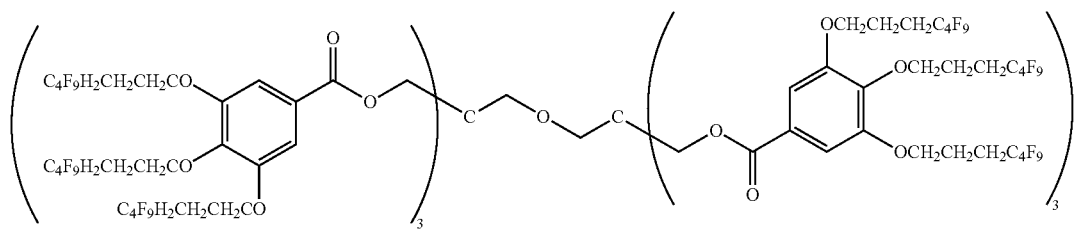
(28)
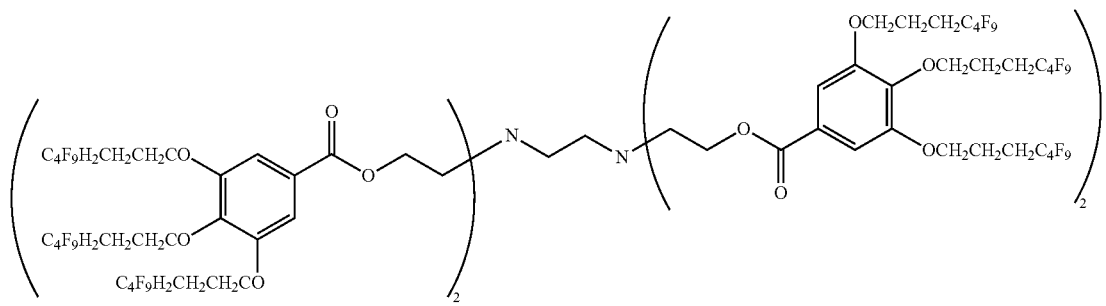
(29)
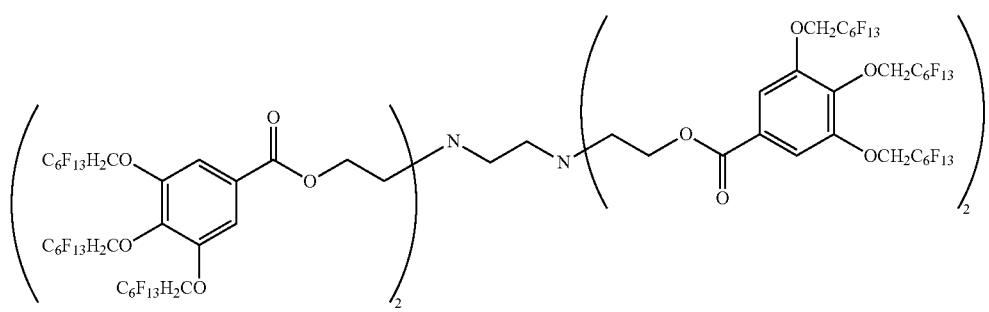
(30)
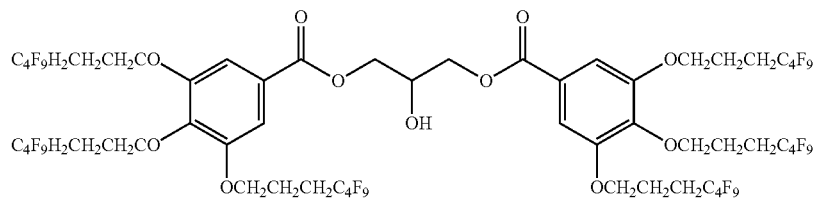
(31)
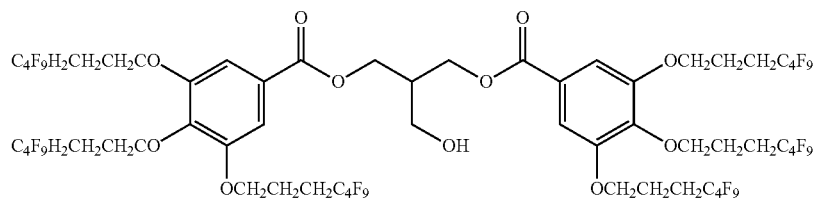
(32)
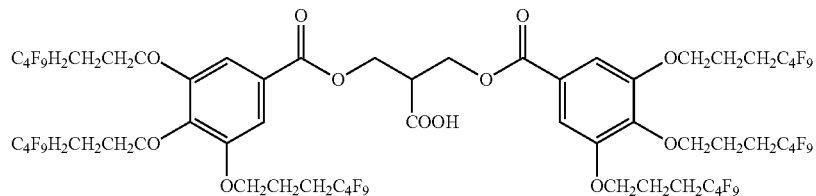
(33)

-continued
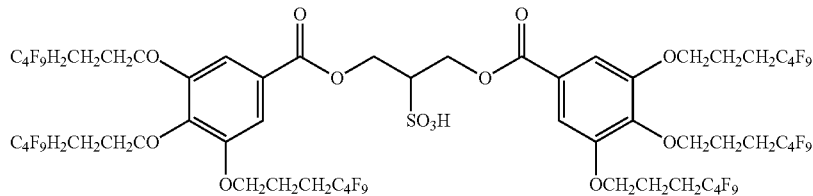
(34)
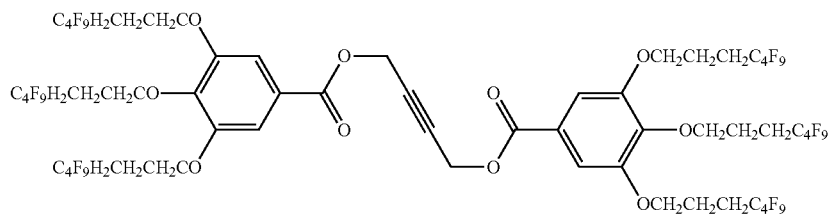
(35)
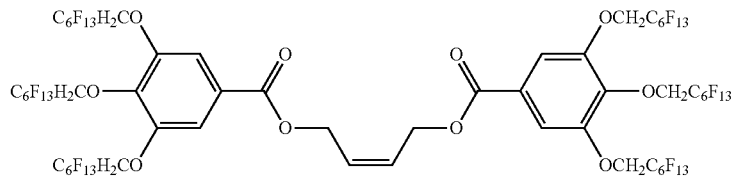
(36)
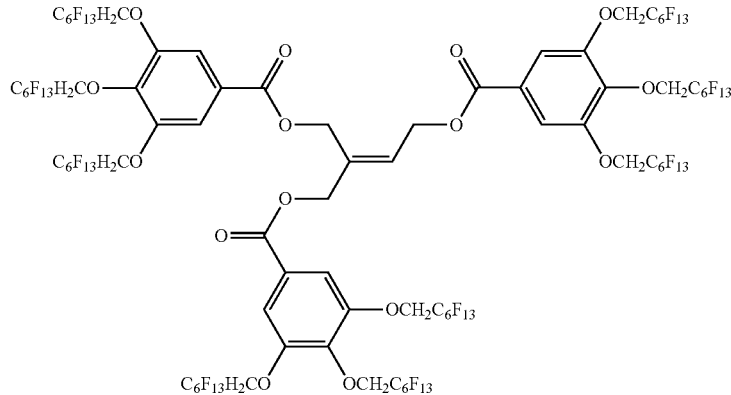
(37)
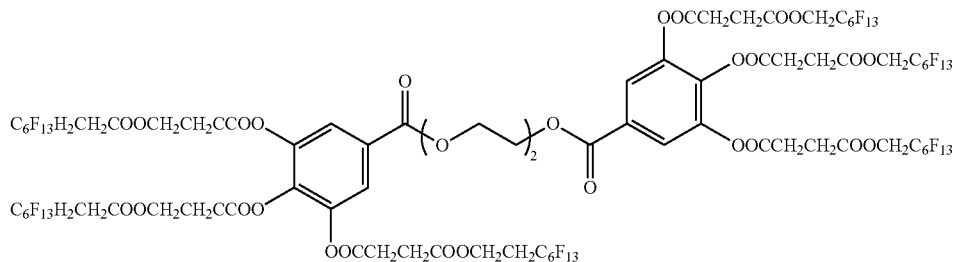
(45)
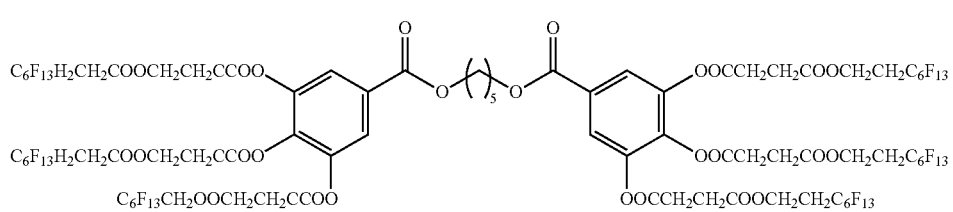
(46)

-continued
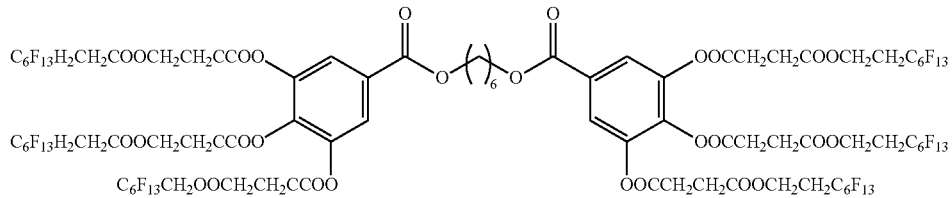
(47)
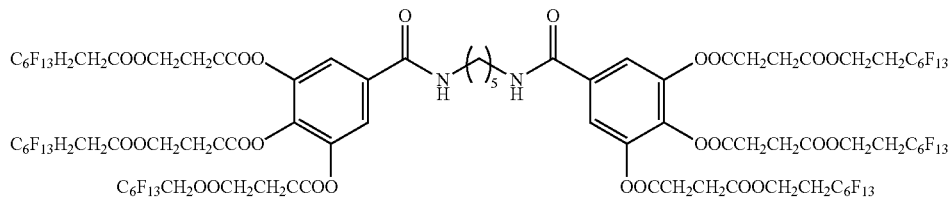
(48)
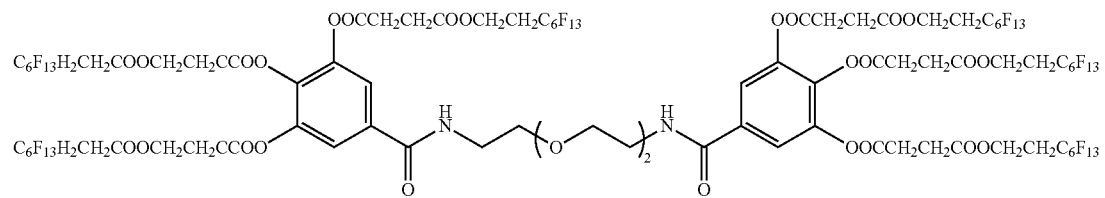
(49)
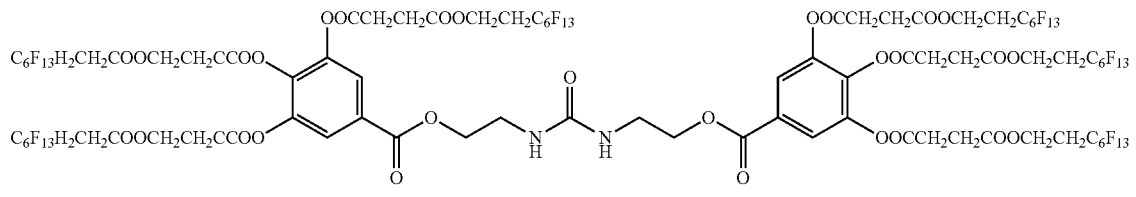
(50)
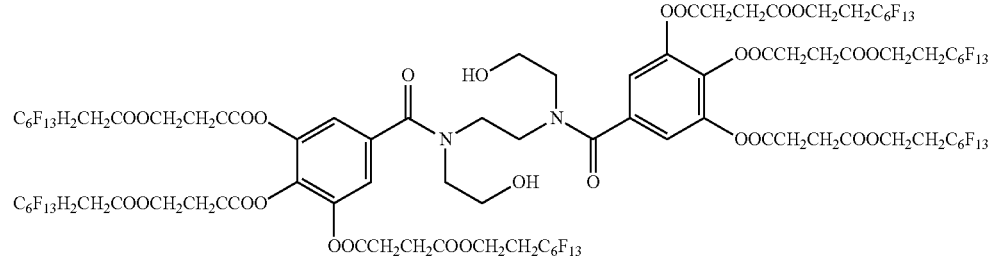
(51)
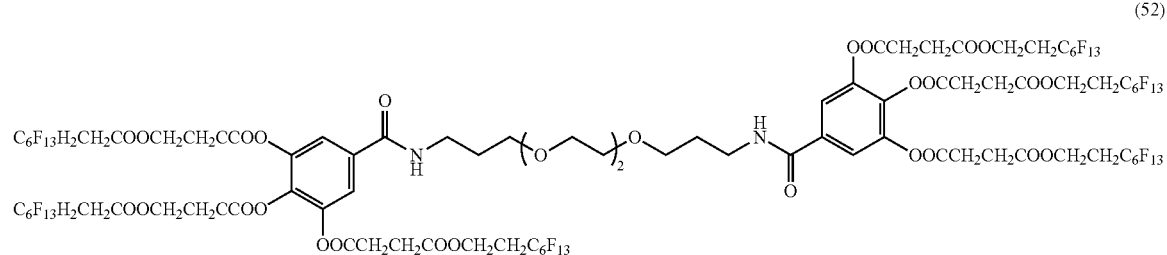
(52)
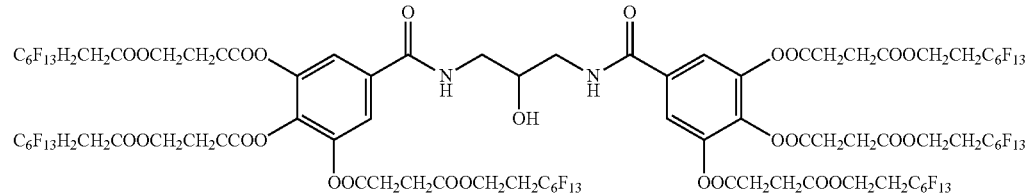
(53)

The compounds represented by formula (1) may be synthesized by appropriately selecting and combining the synthesis methods described in JP-A-2002-129162 and literatures cited in this publication. Other known synthesis methods also may be used in combination, as required.

The compounds represented by the formula (1) may preferably be synthesized, for example, by using the methods described below in Examples of this specification.

The liquid crystal composition of the present invention may use two or more of the compounds represented by formula (1), or may use the compound represented by formula (1) in combination with other liquid crystal alignment promoting agents. The compound represented by formula (1) is used in preferably 0.01 to 20 mass % of the amount of the liquid crystal molecule. More preferably, the compound represented by formula (1) is used in 0.1 to 5 mass % of the liquid crystal molecule. In some cases, the compound represented by formula (1) may preferably be used in 0.15 to 3 mass % of the liquid crystal molecule.

<Liquid Crystal Molecule>

The liquid crystal composition of the present invention includes a liquid crystal molecule.

The liquid crystal molecule is preferably a polymerizable liquid crystal molecule having a polymerizable group.

In the liquid crystal composition of the present invention, one or more polymerizable liquid crystal molecules and one or more non-polymerizable liquid crystal molecules may be used in combination.

The polymerizable liquid crystal molecule is preferably a discotic liquid crystal molecule, or a rod-like liquid crystal molecule.

Discotic liquid crystal molecules are described in various literatures (C. Destrade et al., *Mol. Crysr. Liq. Cryst.*, vol. 71, page 111 (1981); The Chemical Society of Japan, *Kikan Kagaku Sousetsu*, No. 22, Liquid Crystal Chemistry, Chapter 5, Chapter 10, Section 2 (1994); B. Kohne et al., Angew. Chem. Soc. Chem. Comm., page 1794 (1985); and J. Zhang et al., J. Am. Chem. Soc., vol. 116, page 2655 (1994)). Polymerization of discotic liquid crystal molecules is described in JP-A-8-27284. Polymerizing and fixing a discotic liquid crystal molecule requires binding a substituent polymerizable group to the discotic core of the discotic liquid crystal molecule. However, directly binding a polymerizable group to the discotic core makes it difficult to maintain the alignment state in a polymerization reaction. This is counteracted by introducing a linking group between the discotic core and the polymerizable group. It is accordingly preferable that the discotic liquid crystal molecule having a polymerizable group be a compound represented by the following formula.

$$D(-L^P-Q)d$$

In the formula, D is the discotic core; $L^P$ is a divalent linking group; Q is a polymerizable group; and d is an integer of 4 to 12. Specific examples of the discotic core (D) in the formula are given below. In the following specific examples, LQ (or QL) means a combination of a divalent linking group ($L^P$) and a polymerizable group (Q). Triphenylene (D4) is particularly preferred in the following specific examples.

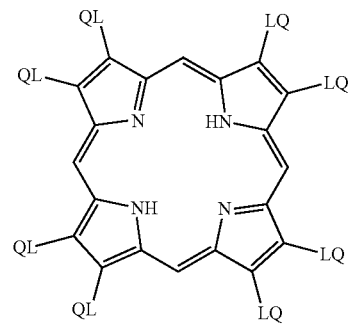
(D1)

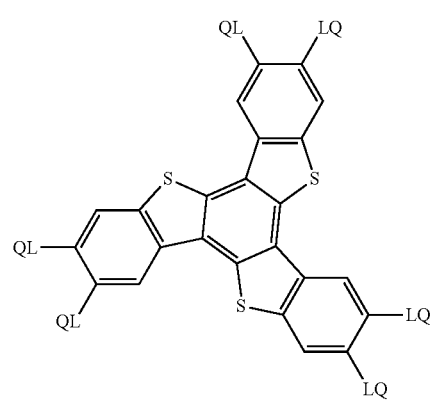
(D2)

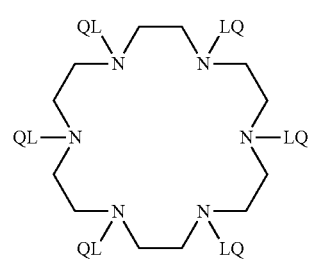
(D3)

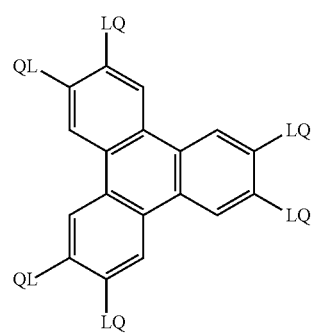
(D4)

(D5)
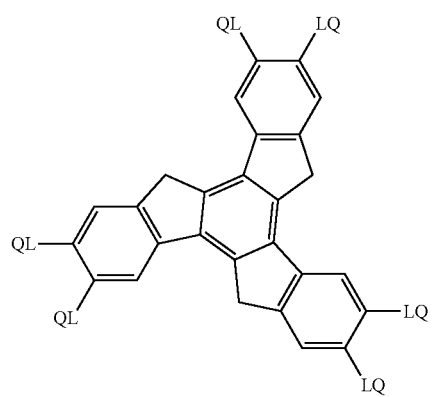
(D6)
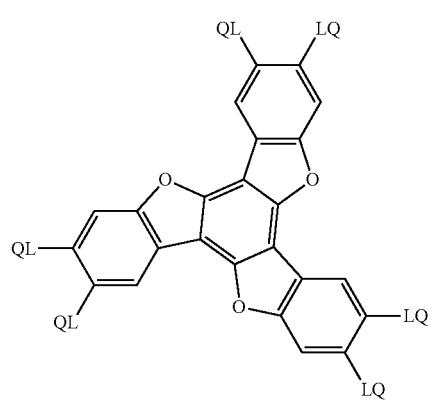
(D7)
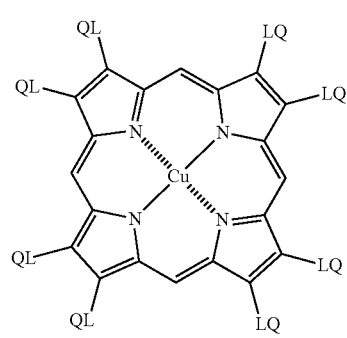
(D8)
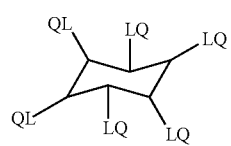
(D9) (D10) (D11)
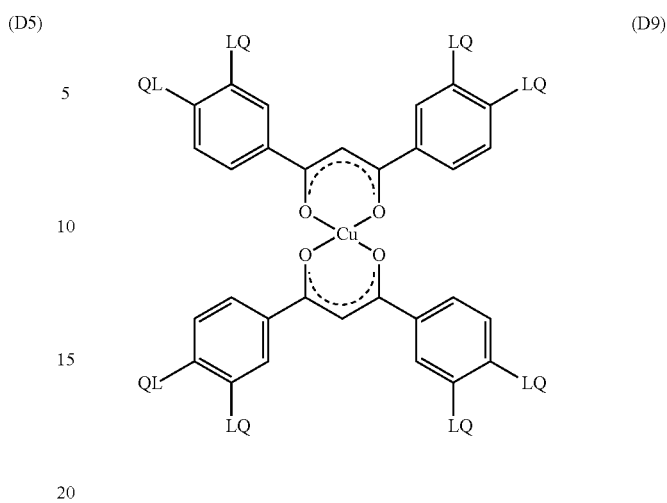

-continued (D12)
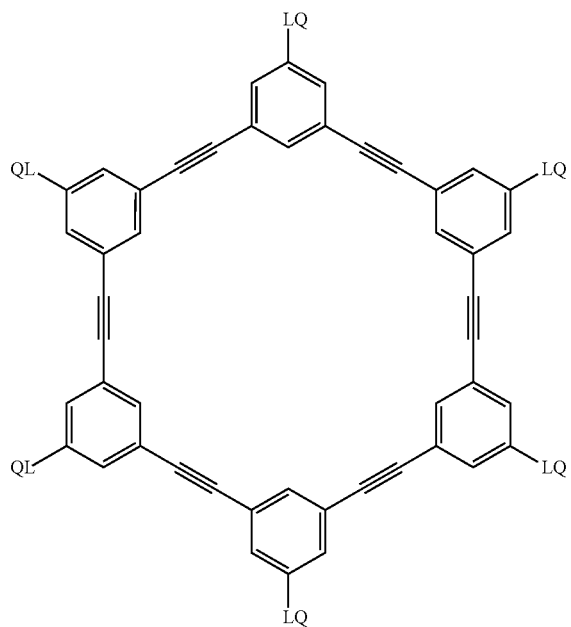

(D13)
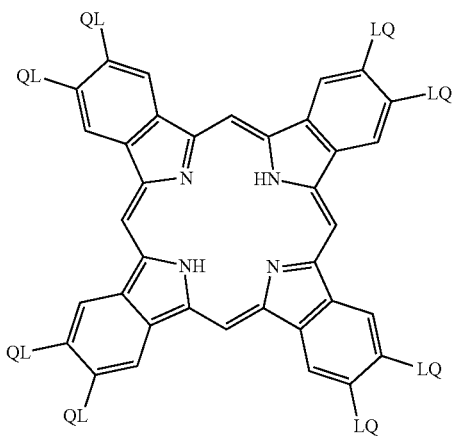

(D14)
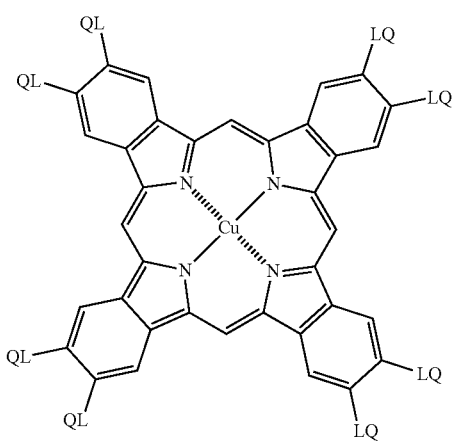

-continued (D15)
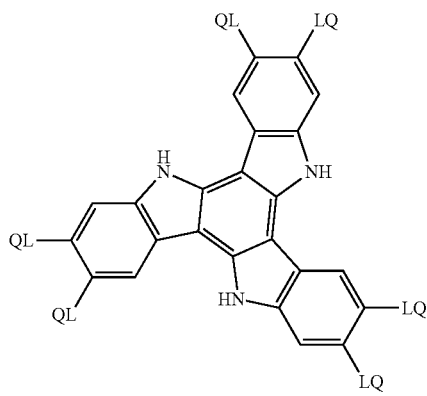

Paragraphs [0161] to [0171] of JP-A-2002-129162 may be referred to for details and the preferred ranges of the linking group $L^D$ and the polymerizable group Q.

Preferred for use as the polymerizable rod-like liquid crystal molecule are, for example, azomethines, azoxys, cyanobiphenyls, cyanophenyl esters, benzoic acid esters, cyclohexane carboxylic acid phenyl esters, cyanophenyl cyclohexanes, cyano-substituted phenylpyrimidines, alkoxy-substituted phenylpyrimidines, phenyldioxanes, tolans, and alkenylcyclohexylbenzonitriles.

The birefringence of the polymerizable rod-like liquid crystal molecule is preferably 0.001 to 0.7. Paragraph [0169] of JP-A-2002-129162 may be referred to for specific examples of the polymerizable group. The rod-like liquid crystal molecule preferably has a substantially symmetrical molecular structure with respect to the short axis direction. It is therefore preferable that the molecule has polymerizable groups at the both ends of the rod-like molecular structure. Specific examples of the rod-like liquid crystal molecule are given below.

(N1)
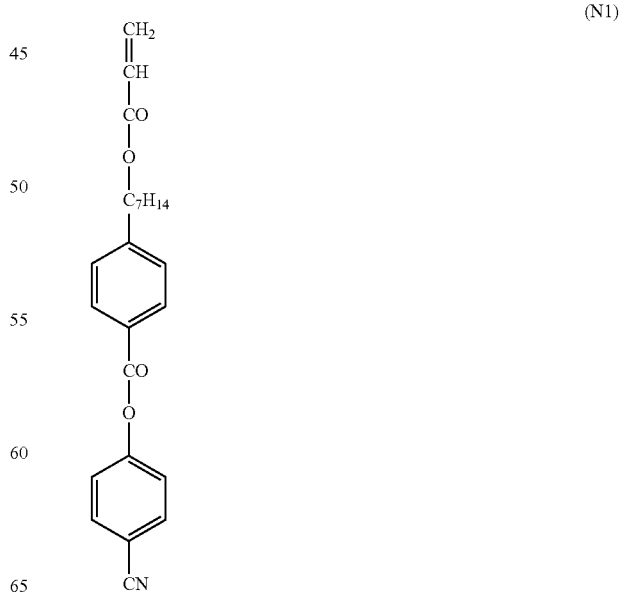

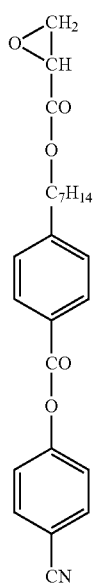 (N2)
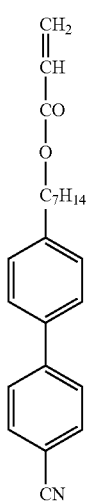 (N3)
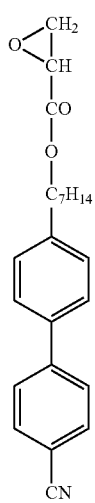 (N4)
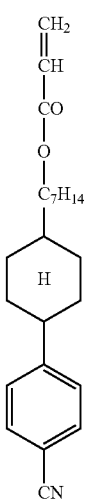 (N5)
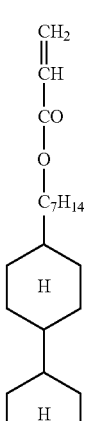 (N6)
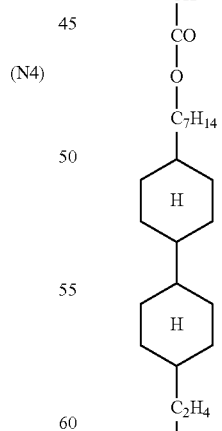 (N7)

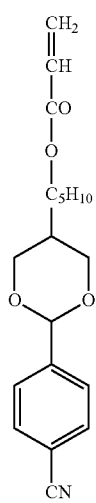 (N8)
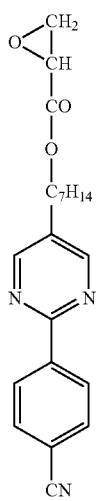 (N9)
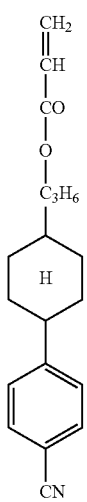 (N10)
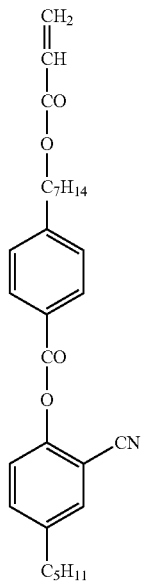 (N11)
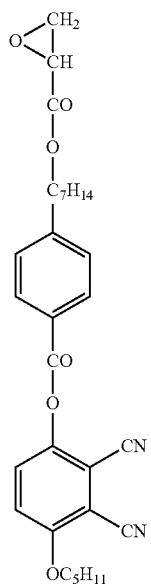 (N12)

(N13)
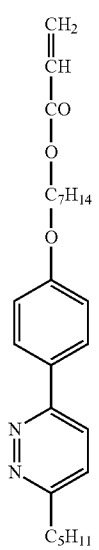
(N14)
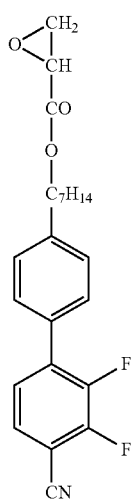
(N15)
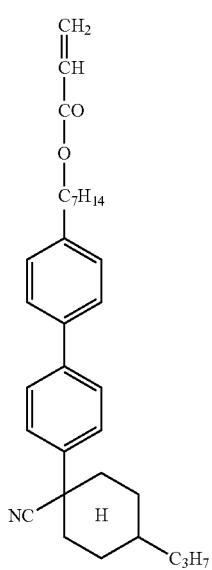
(N16)
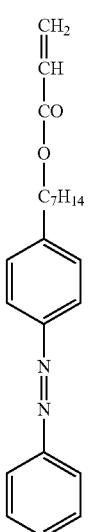
(N17)
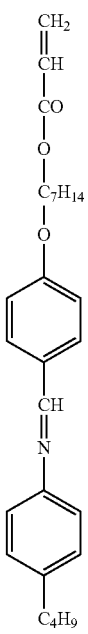

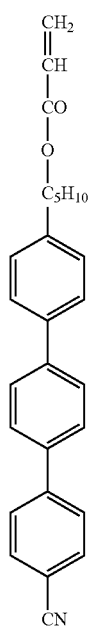 (N18)
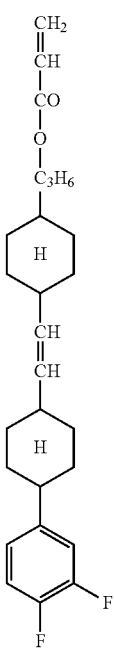 (N20)
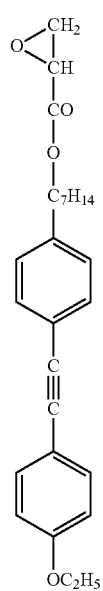 (N19)
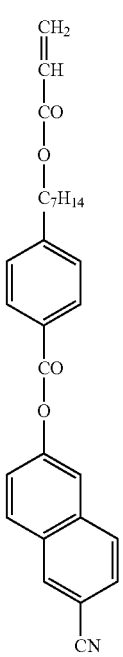 (N21)

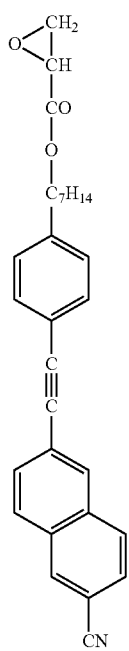 (N22)
 (N23)
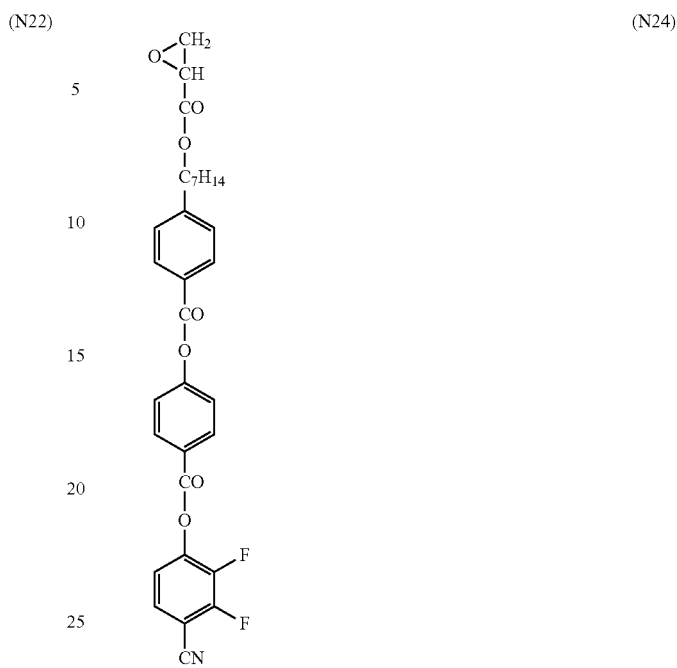

(N26)
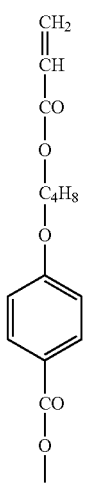
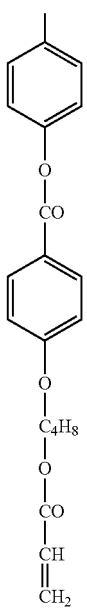
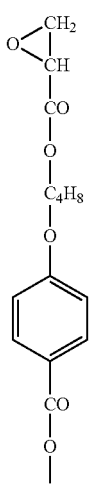
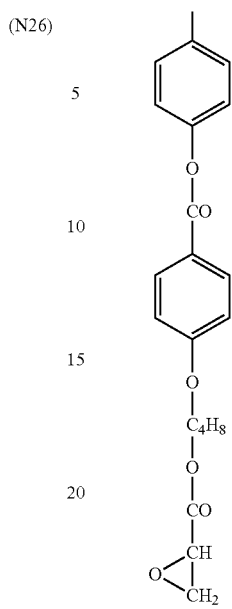
(N27)
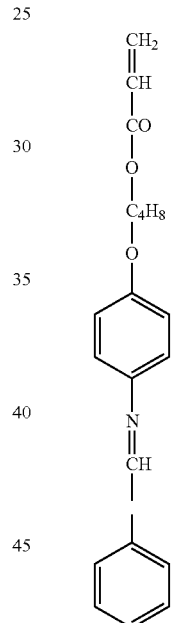
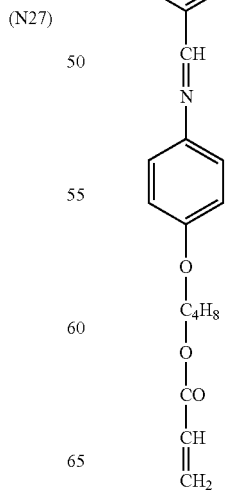
(N28)

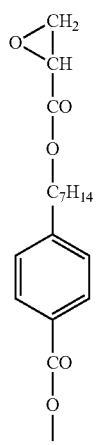
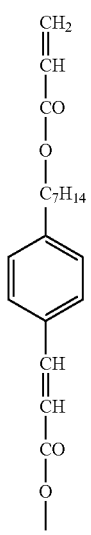
(N29)
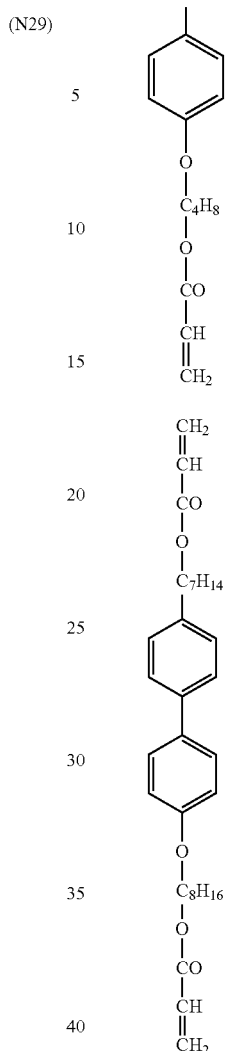
(N30)
(N31)
(N32)
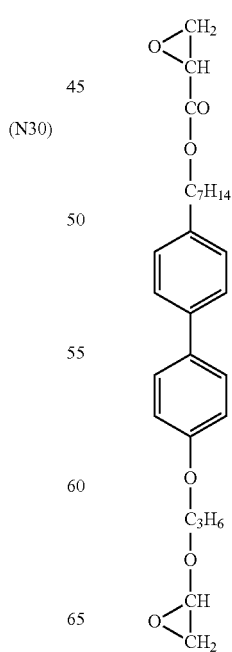

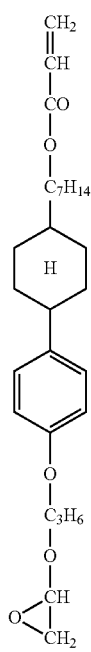
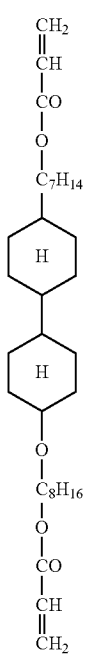
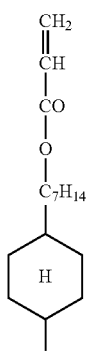
(N33)
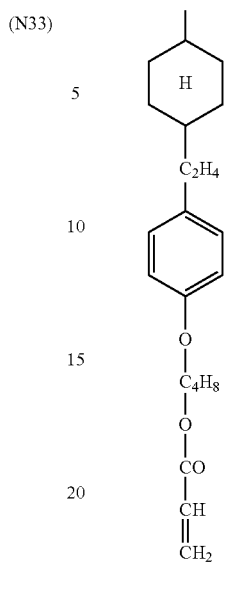
(N34)
(N35)
(N36)
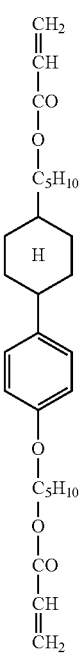

(N37)
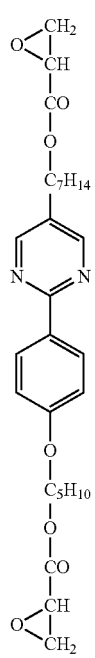
(N39)
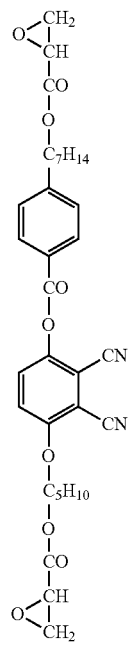
(N40)
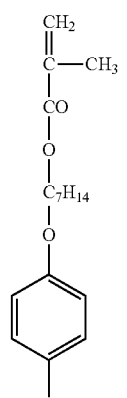
(N38)
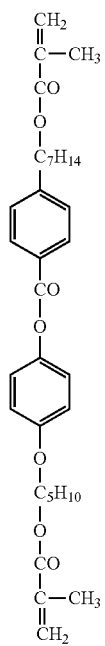
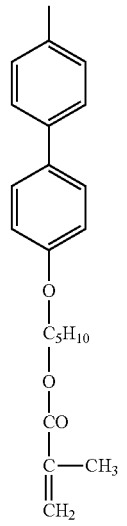

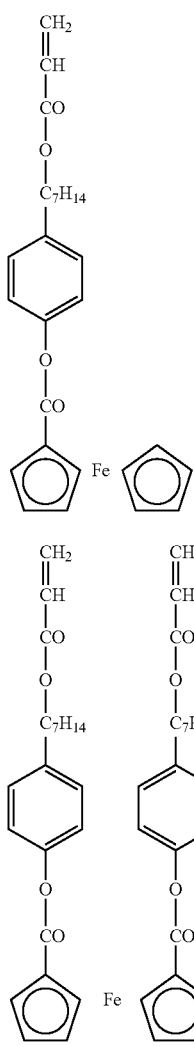
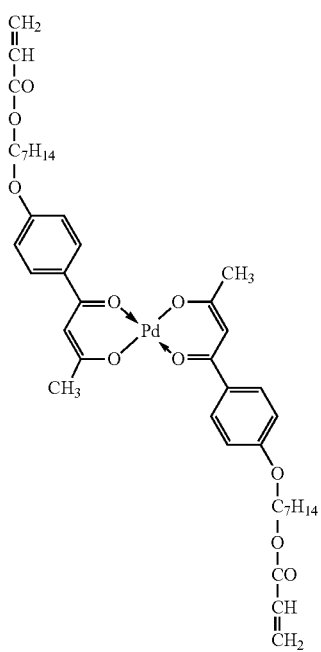
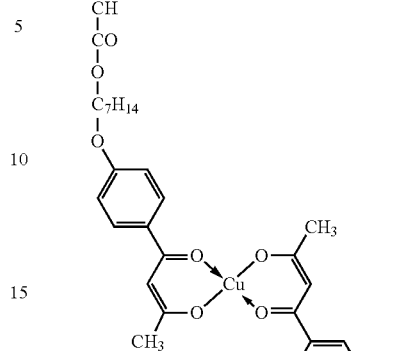
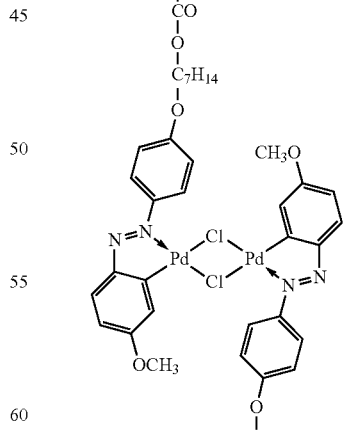

(N46)
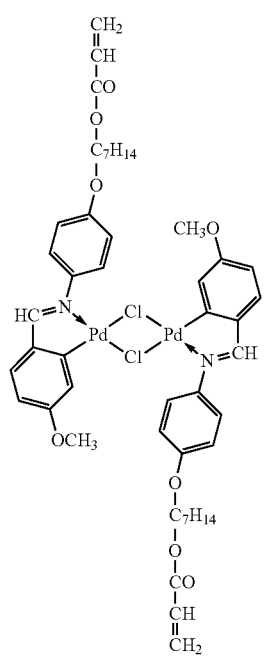
(N47)
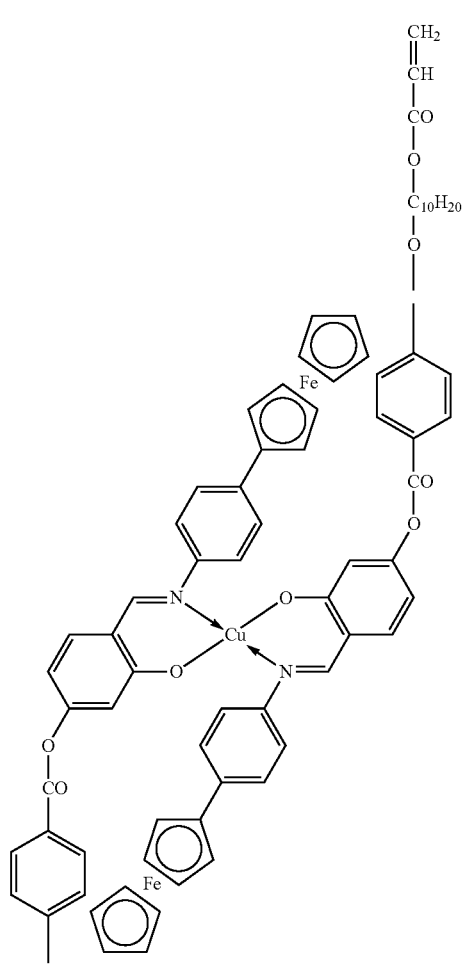
(N48)
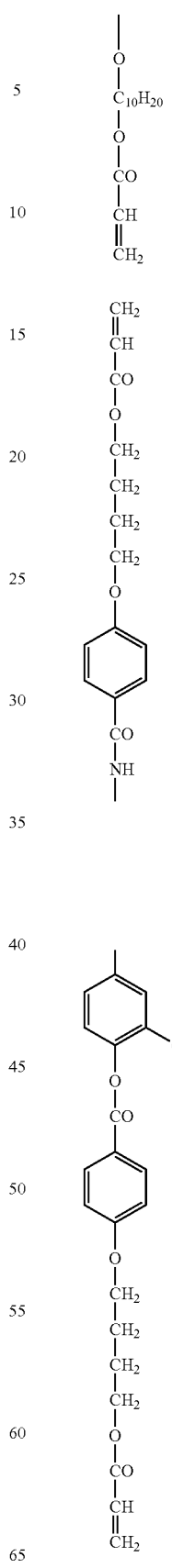

(N49)
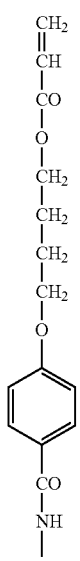
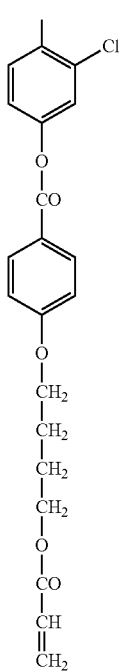
(N50)
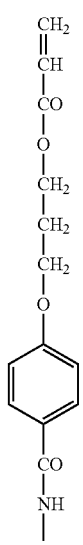
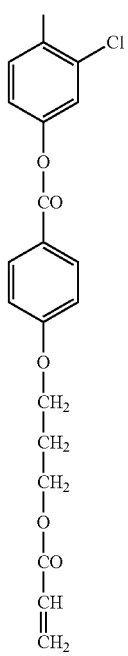

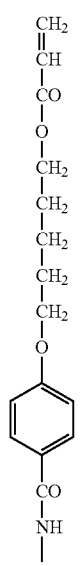 (N51)
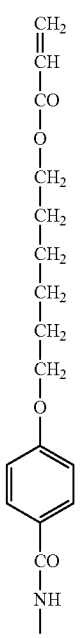 (N52)
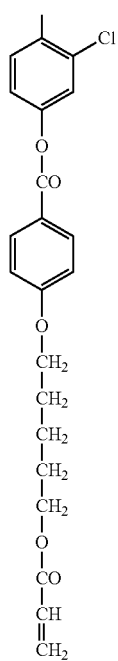
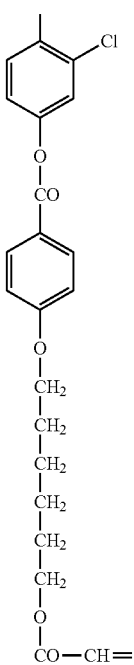

(N53)
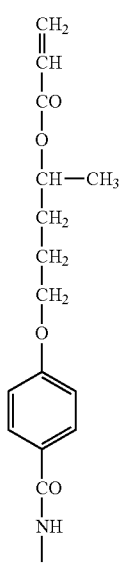
(N54)
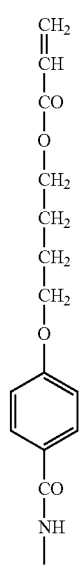
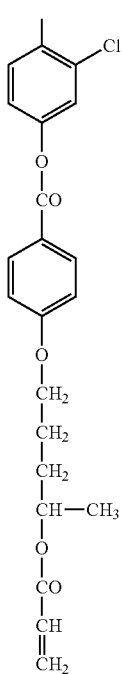
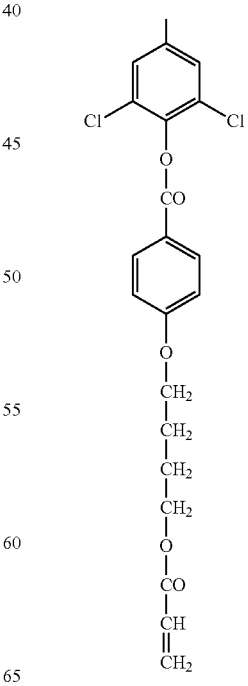

(N55)
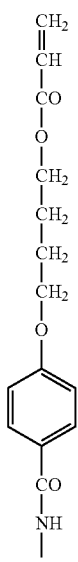
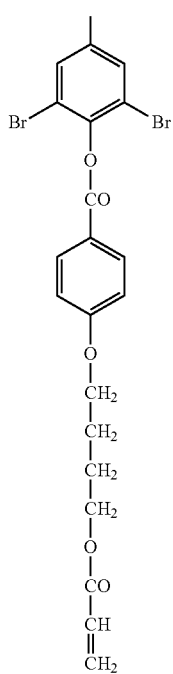
(N56)
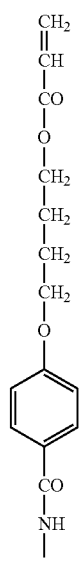
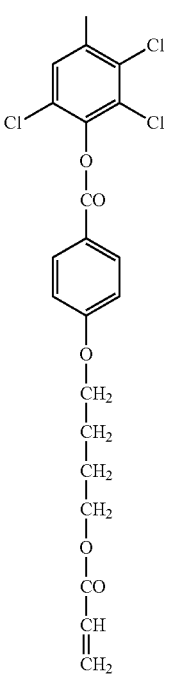

(N57)
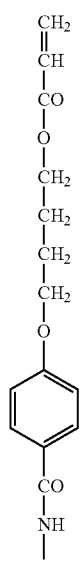
(N58)
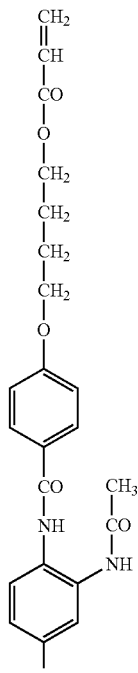
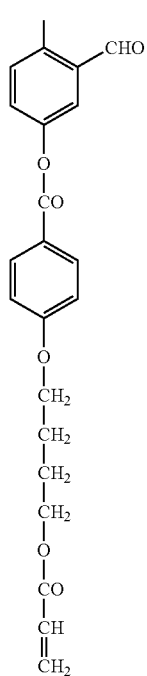
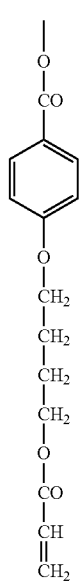

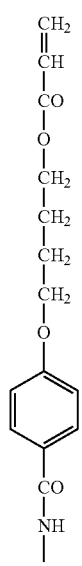 (N59)
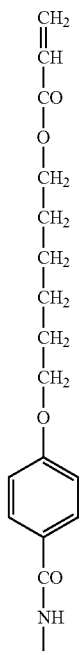 (N60)
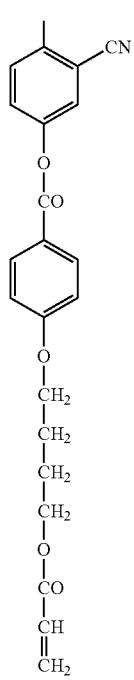
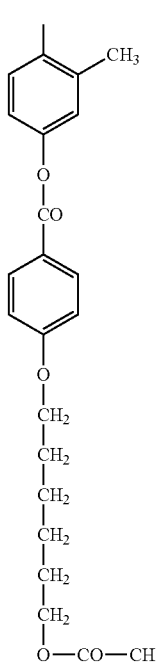

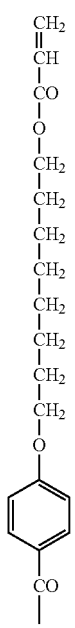 (N61)
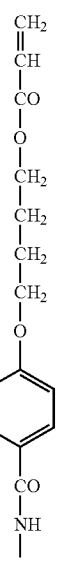 (N62)
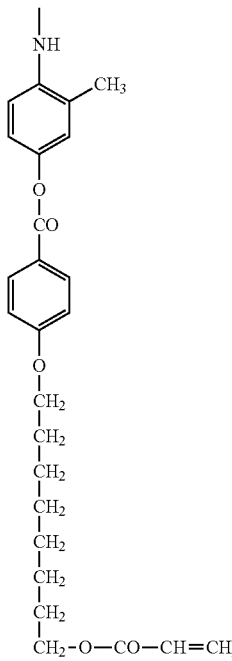
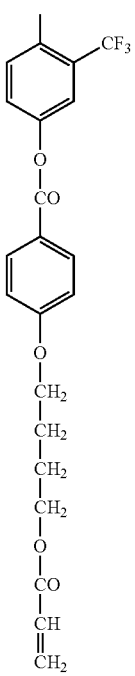

(N63)
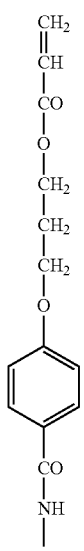
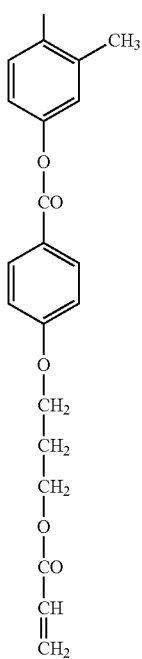
(N64)
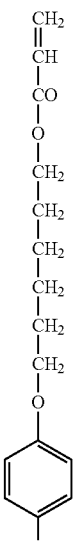
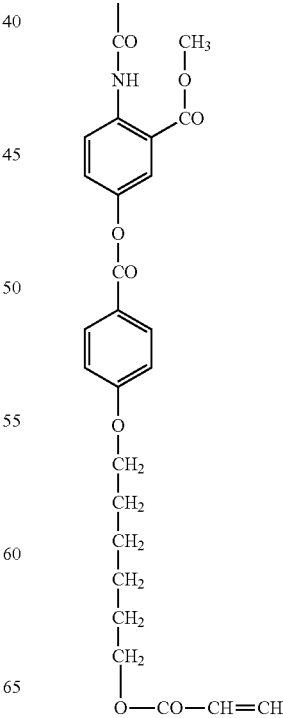

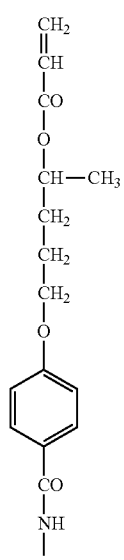
(N65)
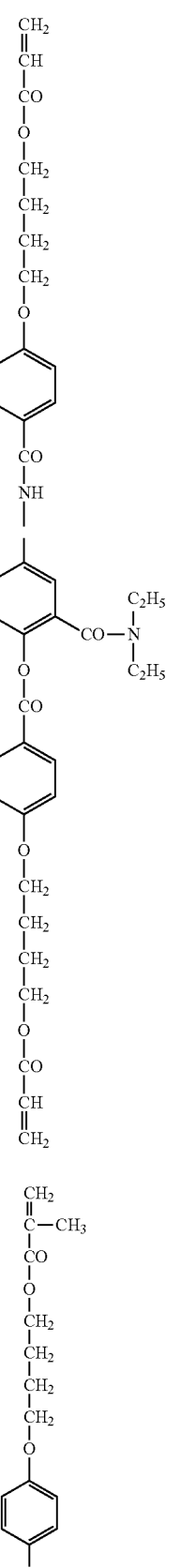
(N66)
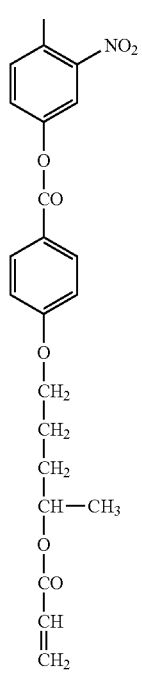
(N67)

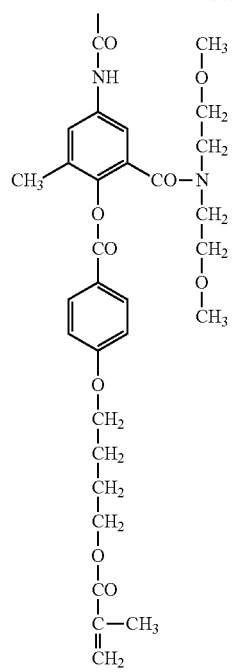
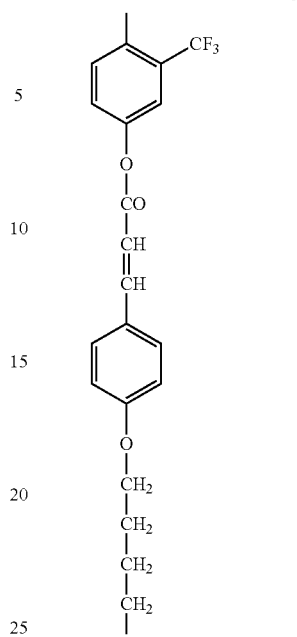
(N68)
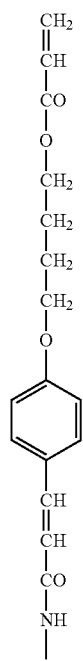
(N69)
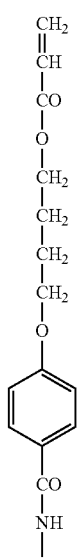

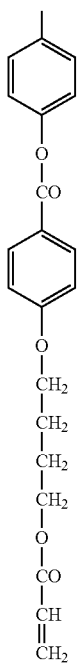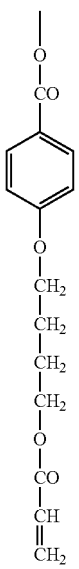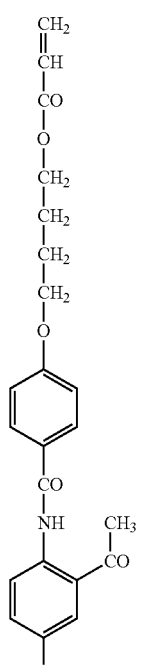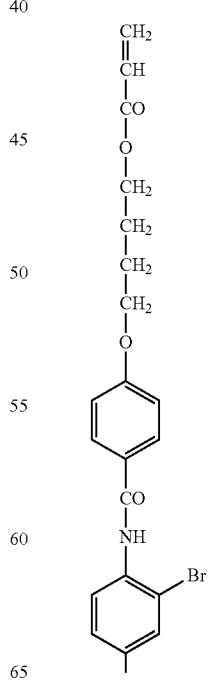
(N70)
(N71)

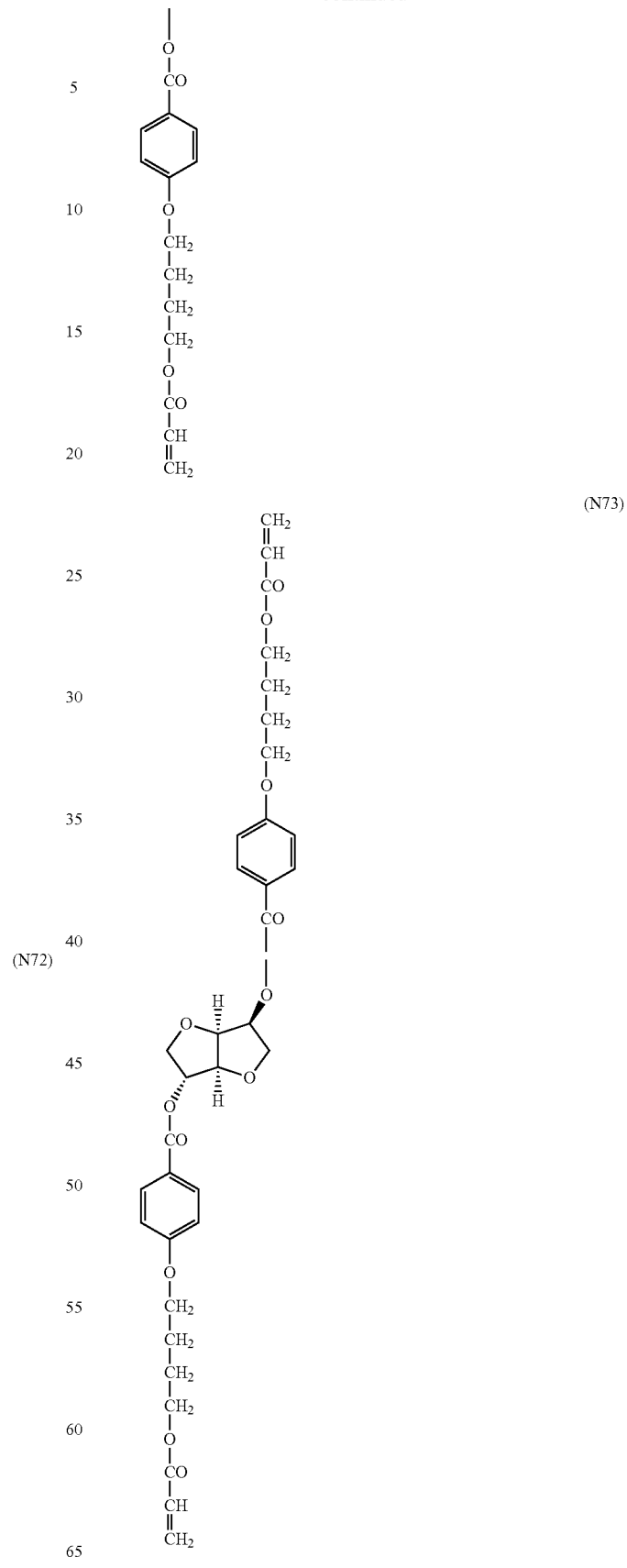
(N72)
(N73)

<Other Additives>

The liquid crystal composition may include a solvent, an asymmetric carbon atom-containing compound, a polymerization initiator (described later), and other additives (for example, cellulose ester), as required, in addition to the polymerizable liquid crystal molecule, and the compound represented by formula (1).

Optically Active Compound (Chiral Agent):

The liquid crystal composition is preferably one that shows a cholesteric liquid crystal phase, and preferably contains an optically active compound to this end. Note, however, that when the rod-like liquid crystal compound is a molecule with an asymmetric carbon atom, a cholesteric liquid crystal phase may stably form without adding an optically active compound. The optically active compounds maybe selected from various known chiral agents (for example, those described in Liquid Crystal Device Handbook, Chapter 3, Section 4-3, TN and STN Chiral Agents, p. 199, Japan Society for the Promotion of Science, 142nd Committee, 1989). The optically active compounds typically include an asymmetric carbon atom; however, axially asymmetric compounds or planar asymmetric compounds containing no asymmetric carbon atom also may be used as chiral agents. Examples of the axially asymmetric compounds and planar asymmetric compounds include binaphthyl, helicene, paracyclophane, and derivatives thereof. The optically active compound (chiral agent) may have a polymerizable group. When the optically active compound, and the rod-like liquid crystal compound used with the optically active compound both have polymerizable groups, the polymerization reaction of the polymerizable optically active compound and the polymerizable rod-like liquid crystal compound can form a polymer that has repeating units derived from the rod-like liquid crystal compound and the optically active compound. In this form of the invention, the polymerizable group of the polymerizable optically active compound is preferably of the same species as that of the polymerizable group of the polymerizable rod-like liquid crystal compound. Accordingly, the polymerizable group of the optically active compound is preferably an unsaturated polymerizable group, an epoxy group, or an aziridinyl group, more preferably an unsaturated polymerizable group, particularly preferably an ethylenic unsaturated polymerizable group.

The optically active compound may be a liquid crystal compound.

The optically active compound contained in the liquid crystal composition is preferably 1 to 30 mol % of the liquid crystal compound used with the optically active compound. The optically active compound should preferably be used in smaller amounts because it often prevents the adverse effect of the optically active compound on liquid crystallinity. For this reason, the optically active compound used as the chiral agent is preferably a compound with strong twisting power so that twist alignment with the desired helical pitch can be achieved in small amounts. Examples of such chiral agents with strong twisting power include those described in JP-A-2003-287623, and these chiral agents may preferably be used in the present invention.

<Solvent>

An organic solvent is preferably used as the solvent of the liquid crystal composition. Examples of the organic solvent include amides (for example, N,N-dimethylformamide), sulfoxides (for example, dimethylsulfoxide), hetero ring compounds (for example, pyridine), hydrocarbon (for example, benzene, and hexane), alkyl halides (for example, chloroform, and dichloromethane), esters (for example, methyl acetate, and butyl acetate), ketones (for example, acetone, methyl ethyl ketone, and cyclohexanone), and ethers (for example, tetrahydrofuran, and 1,2-dimethoxyethane). Alkyl halides, and ketone are preferred. Two or more organic solvents may be used in combination.

[Film]

A film may be formed by depositing the liquid crystal composition of the present invention, using a method such as coating. Further, an optically anisotropic element may be produced by forming a liquid crystal layer with a liquid crystal composition applied onto an alignment film. Preferably, the film of the present invention shows optical anisotropy.

The liquid crystal composition may be applied by using known methods (for example, extrusion coating, direct gravure coating, reverse gravure coating, die coating, and bar coating). Preferably, the liquid crystal molecules are fixed with the maintained alignment state. The liquid crystal molecules are preferably fixed through a polymerization reaction of the polymerizable group (Q) introduced to the liquid crystal molecules.

The polymerization reaction includes a thermal polymerization reaction that uses a thermal polymerization initiator, and a photopolymerization reaction that uses a photopolymerization initiator. A photopolymerization reaction is preferred.

Examples of the photopolymerization initiator include α-carbonyl compounds (described in the specifications of U.S. Pat. Nos. 2,367,661, and 2,367,670), acyloin ethers (described in the specification of U.S. Pat. No. 2,448,828), α-hydrocarbon-substituted aromatic acyloin compounds (described in the specification of U.S. Pat. No. 2,722,512), polynuclear quinone compounds (described in the specifications of U.S. Pat. Nos. 3,046,127 and 2,951,758), combinations of triarylimidazole dimer and p-aminophenylketone (described in the specification of U.S. Pat. No. 3,549,367), acridine and phenazine compounds (described in the specifications of JP-A-60-105667 and U.S. Pat. No. 4,239,850), oxadiazole compounds (described in the specification of U.S. Pat. No. 4,212,970), and acylphosphine oxide compounds (described in the specifications of JP-B-63-40799, JP-B-5-29234, JP-A-10-95788, and JP-A-10-29997).

The photopolymerization initiator is used in preferably 0.01 to 20 mass %, more preferably 0.5 to 5 mass % of the solid content of the coating liquid. Preferably, ultraviolet light is used for the polymerizing photoirradiation of the discotic liquid crystal molecules. Irradiation energy is preferably 20 mJ/cm$^2$ to 50 J/cm$^2$, more preferably 100 to 800 mJ/cm$^2$. The photoirradiation may be performed under heated conditions to promote the photopolymerization reaction.

The thickness is preferably 0.1 to 50 μm, more preferably 1 to 30 μm, most preferably 2 to 20 μm. The total applied amount of the compound represented by formula (1) in the liquid crystal layer (the applied amount of the liquid crystal alignment promoting agent) is preferably 0.1 to 500 mg/m$^2$, more preferably 0.5 to 450 mg/m$^2$, further preferably 0.75 to 400 mg/m$^2$, most preferably 1.0 to 350 mg/m$^2$.

(Selective Reflection Characteristic)

The film of the present invention may preferably be a layer formed by fixing the cholesteric liquid crystal phase of the liquid crystal composition of the present invention. In this case, the film more preferably shows a selective reflection characteristic, particularly preferably a selective reflection characteristic in the infrared wavelength region. Such light reflecting layers formed by fixing the cholesteric liquid crystal phase are described in detail in the methods of JP-A-2011-107178 and JP-A-2011-018037, and may preferably be used in the present invention.

(Laminate)

The film of the present invention may preferably be a laminate of more than one layer formed by fixing the cholesteric liquid crystal phase of the liquid crystal composition of the present invention. The liquid crystal composition of the present invention has desirable lamination, and easily enables forming such a laminate.

[Alignment Film]

The alignment film may be provided by using various means, including rubbing of an organic compound (preferably, a polymer), oblique vapor deposition of an inorganic compound, formation of a layer with microgrooves, and accumulation of an organic compound (for example, ω-tricosanoic acid, dioctadecyl methyl ammonium chloride, and methyl stearate) using the Langmuir-Blodgett technique (LB film). Alignment films that develop an alignment function under an applied electric field, an applied magnetic field, or photoirradiation are also known. An alignment film formed by rubbing a polymer is particularly preferable. Rubbing is performed by rubbing a polymer layer surface with a paper or a fabric in certain directions several times. The type of the polymer used for the alignment film is decided according to the alignment (particularly, the average tilt angle) of the liquid crystal molecules. A polymer (common alignment film polymer) that does not lower the surface energy of the alignment film is used to horizontally (average tilt angle: 0 to 50°) align the liquid crystal molecules, whereas a polymer that lowers the surface energy of the alignment film is used to vertically (average tilt angle: 50 to 90°) align the liquid crystal molecules. In order to lower the surface energy of an alignment film, preferably, a hydrocarbon group having 10 to 100 carbon atoms is introduced to the polymer side chain.

Specific polymers are described in literatures dealing with optical compensation sheets that use various liquid crystal molecules for different display modes. The thickness of the alignment film is preferably 0.01 to 5 μm, more preferably 0.05 to 1 μm. A liquid crystal layer may be transferred onto a transparent support after aligning the liquid crystal molecules of an optically anisotropic layer with an alignment film. The liquid crystal molecules fixed in the alignment state can remain aligned without the alignment film. Rubbing is not required, and the alignment film is unnecessary when the average tilt angle is less than 5°. However, an alignment film (JP-A-9-152509) that forms a chemical bond with the liquid crystal molecules at the interface may be used to improve the adhesion between the liquid crystal molecules and the transparent support. Rubbing may be omitted when such an alignment film is used to improve adhesion. When two liquid crystal layers are provided on the same side of the transparent support, the liquid crystal layer formed on the transparent support may serve as an alignment film for the overlying liquid crystal layer.

[Transparent Support]

The film of the present invention and an optically anisotropic element having the film of the present invention may have a transparent support. The transparent support is a glass plate, or a polymer film, preferably a polymer film. The support being transparent means an optical transmittance of 80% or more. The transparent support is typically an optically isotropic polymer film. Specifically, by "optically isotropic", it means an in-plane retardation (Re) of preferably less than 10 nm, more preferably less than 5 nm. The optically isotropic transparent support has a thicknesswise retardation (Rth) of preferably less than 10 nm, more preferably less than 5 nm. The in-plane retardation (Re) and the thicknesswise retardation (Rth) of the transparent support are defined by the following equations.

$$Re=(nx-ny)\times d$$

$$Rth=[\{(nx+ny)/2\}-nz]\times d$$

In the formulae, nx and ny are the in-plane refractive indices of the transparent support, nz is the thicknesswise refractive index of the transparent support, and d is the thickness of the transparent support.

The transparent support may be an optically anisotropic polymer film. In this case, the transparent support preferably has an optically uniaxial property, or an optically biaxial property. In the case of an optically uniaxial support, the support may be optically positive (the refractive index of the optical axis direction being greater than the refractive index of the direction perpendicular to the optical axis), or negative (the refractive index of the optical axis direction being smaller than the refractive index of the direction perpendicular to the optical axis). In the case of an optically biaxial support, the refractive indices nx, ny, and nz in the foregoing formulae all take different values (nx≠ny≠nz). The in-plane retardation (Re) of the optically anisotropic transparent support is preferably 10 to 1,000 nm, more preferably 15 to 300 nm, most preferably 20 to 200 nm. The thicknesswise retardation (Rth) of the optically anisotropic transparent support is preferably 10 to 1,000 nm, more preferably 15 to 300 nm, further preferably 20 to 200 nm.

The material used to form the transparent support depends on whether the transparent support is provided as an optically isotropic support or an optically anisotropic support. In the case of an optically isotropic support, glass or cellulose ester is typically used. In the case of an optically anisotropic support, synthetic polymers (for example, polycarbonate, polysulfone, polyethersulfone, polyacrylate, polymethacrylate, norbornene resin) are used. An optically anisotropic (high retardation) cellulose ester film also may be produced by using the film producing methods described in the specification of European Patent No. 0911656A2, specifically by (1) using a retardation increasing agent, (2) lowering the degree of acetification of cellulose acetate, or (3) using a cooling dissolution method. The transparent support formed of a polymer film is preferably formed by using a solvent casting method.

Preferably, the optically anisotropic transparent support is obtained by drawing a polymer film. The optically uniaxial support may be produced by using a common uniaxial drawing process or a biaxial drawing process. The optically biaxial support is produced preferably through an unbalanced biaxial drawing process. In the unbalanced biaxial drawing, a polymer film is drawn in a certain direction at a certain rate (for example, 3 to 100%, preferably 5 to 30%), and in a direction perpendicular to this direction at a higher rate (for example, to 200%, preferably 10 to 90%). The drawing may be simultaneously performed in two directions. Preferably, the drawing direction (the direction with a higher drawing rate in the case of unbalanced biaxial drawing) and the in-plane slow axis of the drawn film direct in substantially the same direction. The angle between the drawing direction and the slow axis is preferably less than 10°, more preferably less than 5°, further preferably less than 3°.

The thickness of the transparent support is preferably 10 to 500 μm, more preferably 50 to 200 μm. The transparent support may be subjected to a surface treatment (for example, glow discharge process, corona discharge process, ultraviolet (UV) treatment, and flame treatment) to improve the adhesion between the transparent support and the overlying layer (adhesive layer, alignment film, or optically anisotropic layer). A ultraviolet absorber maybe added to the transparent support. An adhesive layer (primer layer) may be provided on the transparent support. The adhesive layer is described in JP-A-7-333433. The thickness of the adhesive layer is preferably 0.1 to 2 μm, more preferably 0.2 to 1 μm.

EXAMPLES

The features of the present invention are described below in greater detail using Examples and Comparative Examples. Materials, amounts, proportions, and the contents and the procedures of the processes used in the following Examples may be appropriately varied, provided that such changes do not depart from the gist of the present invention. Accordingly, the scope of the present invention should not be narrowly interpreted within the limits of the concrete examples described below.

Example 1

Compound (1) was synthesized by using the following route.

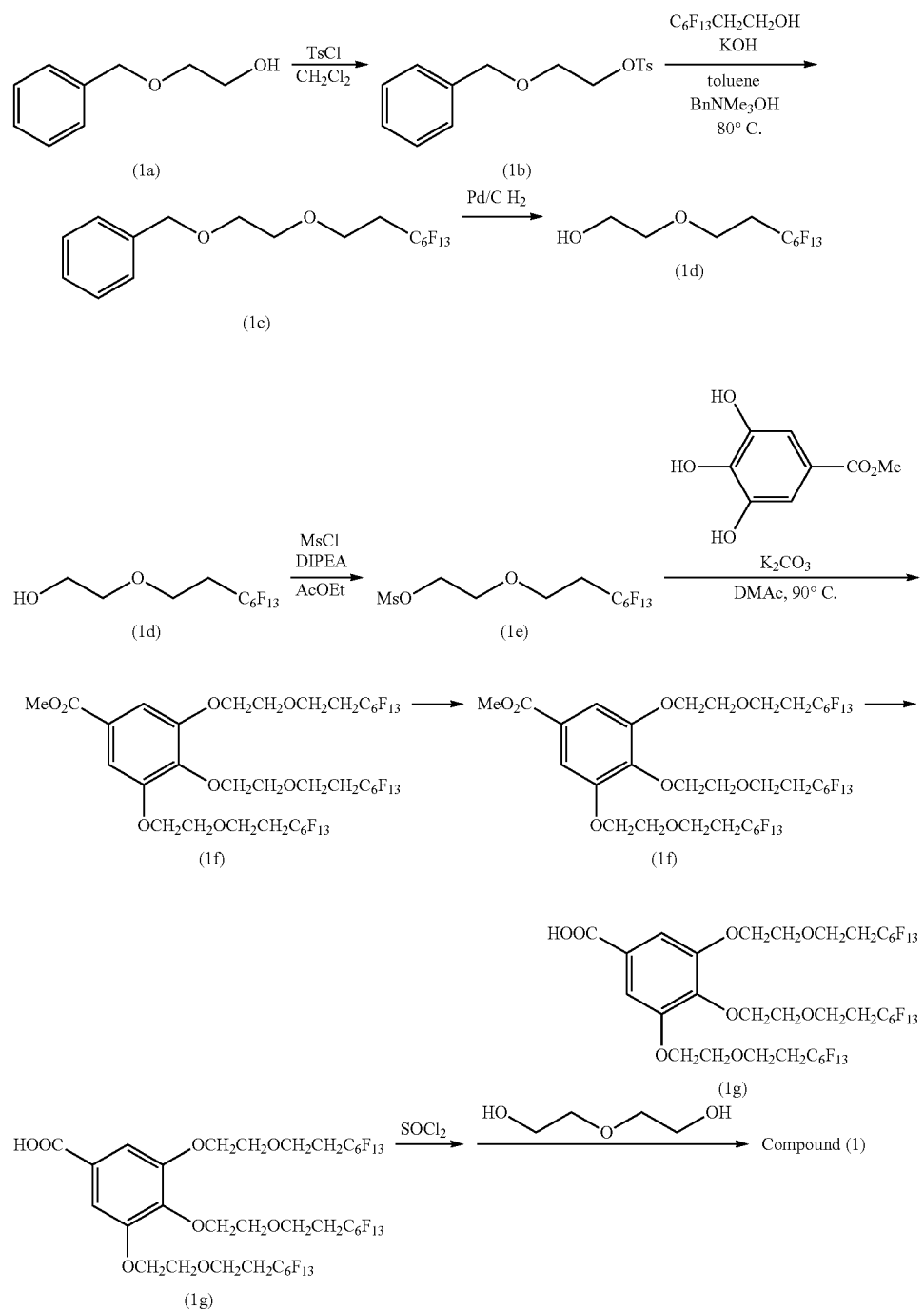

(1-1) Synthesis of Tosyl Derivative (1b)

Alcohol (1a; 45.7 ml, 300 mmol) and para-toluenesulfonyl chloride (60.1 g, 315 mmol) were reacted in 120 ml of methylene chloride under ice-cooled condition for 1 hour. The reaction mixture was subjected to a separation procedure, and the organic layer was concentrated with an evaporator to obtain a tosyl ether (1b) as a crude yellow liquid. The product was directly used as raw material in the next step without being purified.

$^1$H NMR (300 MHz, CDCl$_3$) δ 2.4 (s, 3H), 3.6 (d, 2H), 4.2 (d, 2H), 4.4 (s, 2H), 7.1-7.4 (d×3, s×1, 7H), 7.8 (d, 2H)

(1-2) Synthesis of Fluorinated Alkyl Ether (1c)

Tosyl derivative (1b; 16.2 g, 50 mmol) and 2-(perfluorohexyl)ethanol (12.1 ml, 55 ml) were added to 100 ml of toluene, and a benzyltrimethylammonium hydroxide aqueous solution (105 ml) was added thereto. After heating the mixture to 70° C. and stirring the mixture for 30 min, a potassium hydroxide aqueous solution (3.1 g/water 20 ml) was added. The mixture was heated to 80° C., and a reaction was allowed for 5 hours. After adding ethyl acetate (100 ml) and water (50 ml) for separation, the resulting liquid was concentrated to obtain ether (1c) as a crude product. The product was directly used as raw material in the next step without being purified.

$^1$H NMR (300 MHz, CDCl$_3$) δ 2.5 (m, 2H), 3.8 (d, 2H), 4.0 (d, 2H), 4.4 (s, 2H), 7.1-7.4 (m, 5H)

(1-3) Synthesis of Alcohol (1d)

Ether (1c; 20.0 g, 40 mmol) was reacted with hydrogen in ethyl acetate (40 ml) in the presence of a palladium catalyst (1.2 g, 5% palladium/activated carbon, Degussa type E 101 O/W 5% Pd, Wako). After the reaction, the palladium catalyst was removed by celite filtration, and the resulting liquid was concentrated to obtain alcohol (1d) as a crude product. The product was directly used as raw material in the next step without being purified.

$^1$H NMR (400 MHz, CDCl$_3$) δ2.4 (m, 2H), 3.6 (d, 2H), 3.7 (d, 2H), 3.8 (d, 2H)

(1-4) Synthesis of Methanesulfonic Acid Ester (1e)

Alcohol (1d; 18.0 g, 45 mmol) was added to 30 ml of ethyl acetate, and the mixture was ice-cooled. Methanesulfonyl chloride (3.8 ml, 49.5 mmol) was then dropped at the maintained temperature of 20° C. or less in the reaction system. Reaction was allowed at room temperature for 3 hours, and the mixture was separated with ethyl acetate and water. The resulting liquid was concentrated to give methanesulfonic acid ester (1e) as a crude product. The product was directly used as raw material in the next step without being purified.

(1-5) Synthesis of Gallic Acid Ester (1f)

Ester (1e; 10.6 g, 21.6 mmol) and methyl gallate ester (1.28 g, 7.0 mmol) were reacted in DMAc (40 ml) at 90° C. in the presence of potassium carbonate (3.0 g, 21.6 mmol). The mixture was subjected to a separation procedure in an ethyl acetate/water system, and the resulting liquid was column purified to obtain an oily gallic acid ester (1f; 8.0 g, 84%).

$^1$H NMR (400 MHz, CDCl$_3$) δ 2.3-2.6 (m, 6H), 3.7-4.0 (m, 15H), 4.2 (m, 6H), 7.4 (s, 2H)

(1-6) Synthesis of Carboxylic Acid (1g)

Ester (1f; 7.8 g, 5.8 mmol) was added to ethanol (40 ml) and water (4 ml). Potassium hydroxide (0.48 g, 8.6 mmol) was added to the solution, and the mixture was heated under reflux for 2 hours. The reaction mixture was separated in an ethyl acetate/water system, and the organic layer was concentrated and solidified to give carboxylic acid (1g; 5.6 g, 72%).

(1-7) Synthesis of Compound (1)

Carboxylic acid (1g; 2.0 g, 1.5 mmol) was reacted with thionyl chloride (0.16 ml, 2.2 mmol) in toluene (10 ml) and a catalytic amount of DMF to produce an acid chloride. After removing the excess thionyl chloride and toluene, THF (5 ml) and a catalytic amount of DMAP were added to the system. THF (5 ml), diisopropylethylamine (0.28 ml), and diethylene glycol (79 mg, 0.75 mmol) were then dropped into the mixture. After a separation procedure with an ethyl acetate/water system, the resulting liquid was concentrated with an evaporator, column purified, and recrystallized in an ethyl acetate/methanol system to give compound (1) (1.4 g, 70%).

$^1$H NMR (300 MHz, CDCl$_3$) δ 2.3-2.5 (m, 12H), 3.7-3.9 (m, 28H), 4.1-4.2 (m, 12H), 4.4-4.5 (m, 4H), 7.3 (s, 4H)

Example 2

Compound (6) was synthesized by using the following route.

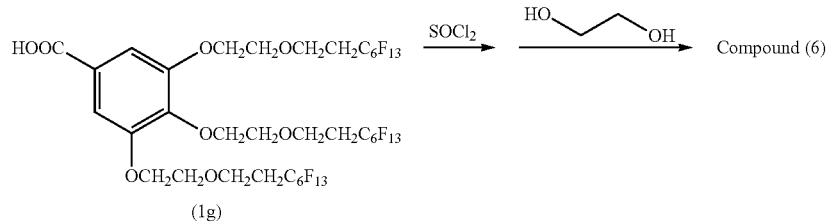

Compound (6) was obtained by using the same procedures used in Example 1, except that the diethylene glycol used in (1-7) for the synthesis of compound (1) was replaced with ethylene glycol.

$^1$H NMR (300 MHz, CDCl$_3$) δ 2.3-2.5 (m, 12H), 3.7-3.9 (m, 24H), 4.1-4.2 (m, 12H), 4.6 (s, 4H), 7.3 (s, 4H)

Example 3

Compound (21) was synthesized by using the following route.

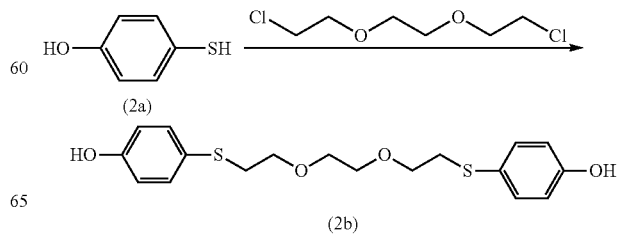

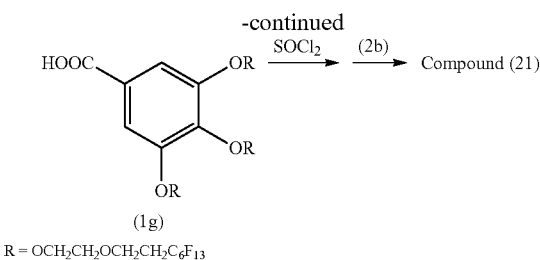

(21-1) Synthesis of Diol (2b)

4-Hydroxythiophenol (1e; 10.0 g, 79.3 mmol) and 1,2-bis(chloroethoxy)ethane (7.06 g, 37.76 mmol) were reacted in DMAc (35 ml) at 50° C. in the presence of potassium carbonate (11.0 g, 79.3 mmol). After a separation procedure with an ethyl acetate/water system, the resulting liquid was column purified to give a crystalline diol (2b; 5.7 g, 42%).

(21-2) Synthesis of Compound (21)

Compound (21) was obtained by using the same procedures used in Example 1, except that the diethylene glycol used in (1-7) for the synthesis of compound (1) was replaced with diol (2b).

$^1$H NMR (300 MHz, CDCl$_3$) δ 2.3-2.5 (m, 12H), 3.1 (t, 4H), 3.6 (s, 4H), 3.7 (t, 4H), 3.8-3.9 (m, 24H), 4.2-4.3 (m, 12H), 7.1 (d, 4H), 7.4 (d, 4H), 7.5 (s, 4H)

Example 4

Compound (24) was synthesized by using the following route.

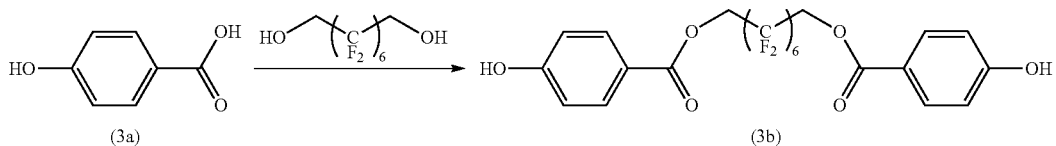

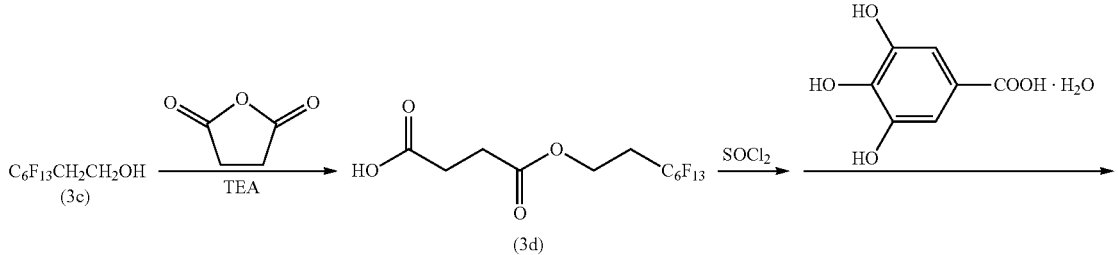

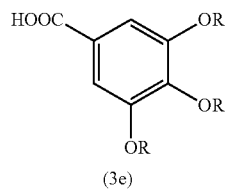

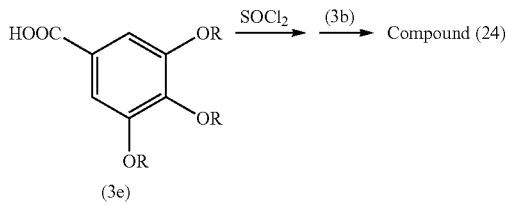

(24-1) Synthesis of Diol (3b)

2,2,3,3,4,4,5,5,6,6,7,7-Dodecafluoro-1,8-octanediol (18.1 g, 50 mmol) and p-hydroxybenzoic acid (3a; 13.8 g, 100 mmol) were reacted in toluene (100 ml) under heat and reflux in the presence of para-toluenesulfonic acid monohydrate (4.8 g, 25 mmol). After a separation procedure with an ethyl acetate/water system, the resulting liquid was column purified to obtain a crystalline diol (3b; 21.1 g, 70%).

(24-2) Synthesis of Compound (24)

Carboxylic acid (3d) can be synthesized from compound (3c) by using the synthesis route of the foregoing scheme according to a known synthesis method. The carboxylic acid (3d) was induced to produce an acid chloride with thionyl chloride, and reacted with gallic acid hydrate to obtain a carboxylic acid (3e). The carboxylic acid (3e) was induced to produce an acid chloride with thionyl chloride, and reacted with the diol (3d) in the presence of DIPEA to give compound (24).

$^1$H NMR (300 MHz, CDCl$_3$) δ 2.4-2.6 (m, 12H), 2.7-2.8 (m, 12H), 2.9-3.1 (m, 12H), 4.4-4.5 (m, 12H), 4.8 (t, 4H), 7.3 (d, 4H), 7.9 (s, 3H), 8.1 (d, 4H)

Example 5

Compound (45) was synthesized by using the following route.

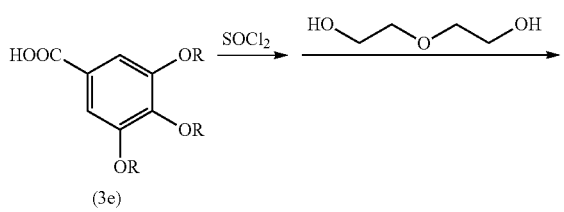

(3e)

Compound (45)

R = OCCH$_2$CH$_2$COOCH$_2$CH$_2$C$_6$F$_{13}$

Compound (45) was obtained by using the same procedures used in Example 4, except that the diol (3d) used in (24-2) for the synthesis of compound (24) was replaced with ethylene glycol.

$^1$H NMR (300 MHz, CDCl$_3$) δ 2.3-2.5 (m, 12H), 2.7-2.8 (m, 12H), 2.8-3.0 (m, 12H), 3.8-3.9 (m, 4H), 4.3-4.4 (m, 12H), 4.4-4.5 (m, 4H), 7.8 (s, 4H)

Example 6

Compound (46) was synthesized by using the following route.

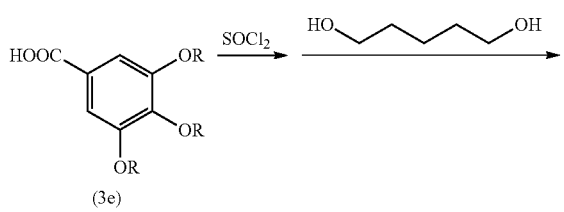

(3e)

Compound (46)

R = OCCH$_2$CH$_2$COOCH$_2$CH$_2$C$_6$F$_{13}$

Compound (46) was obtained by using the same procedures used in Example 4, except that the diol (3d) used in (24-2) for the synthesis of compound (24) was replaced with 1,5-heptanediol.

$^1$H NMR (300 MHz, CDCl$_3$) δ 1.8-1.9 (m, 2H), 2.3-2.5 (m, 12H), 2.7-2.8 (m, 12H), 2.9-3.0 (m, 12H), 4.3-4.4 (m, 4H), 4.4-4.5 (m, 12H), 7.8 (s, 4H)

Example 7

Compound (47) was synthesized by using the following route.

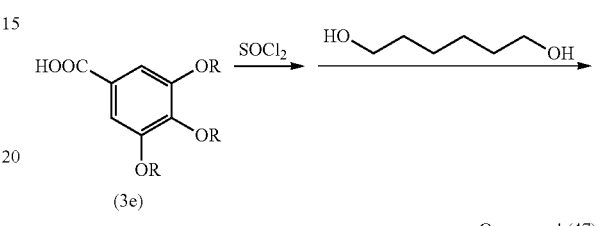

(3e)

Compound (47)

R = OCCH$_2$CH$_2$COOCH$_2$CH$_2$C$_6$F$_{13}$

Compound (47) was obtained by using the same procedures used in Example 4, except that the diol (3d) used in (24-2) for the synthesis of compound (24) was replaced with 1,6-hexanediol.

$^1$H NMR (300 MHz, CDCl$_3$) δ 1.8-1.9 (m, 4H), 2.4-2.6 (m, 12H), 2.7-2.8 (m, 12H), 2.9-3.0 (m, 12H), 4.3-4.4 (m, 4H), 4.4-4.5 (m, 12H), 7.8 (s, 4H)

Example 7

Compound (48) was synthesized by using the following route.

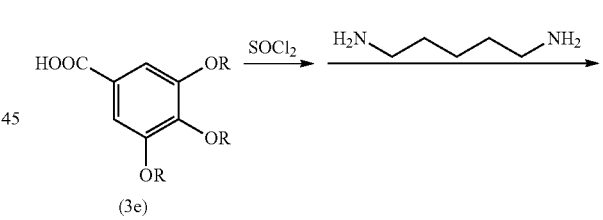

(3e)

Compound (48)

R = OCCH$_2$CH$_2$COOCH$_2$CH$_2$C$_6$F$_{13}$

Compound (48) was obtained by using the same procedures used in Example 4, except that the diol (3d) used in (24-2) for the synthesis of compound (24) was replaced with 1,5-diaminopentane.

$^1$H NMR (300 MHz, CDCl$_3$) δ 1.4-1.5 (m, 2H), 1.6-1.7 (m, 4H), 2.4-2.6 (m, 12H), 2.7-2.8 (m, 12H), 2.8-3.0 (m, 12H), 3.4-3.5 (m, 4H), 4.3-4.5 (m, 12H), 6.3 (t, 2H), 7.6 (s, 4H)

Example 7

Compound (49) was synthesized by using the following route.

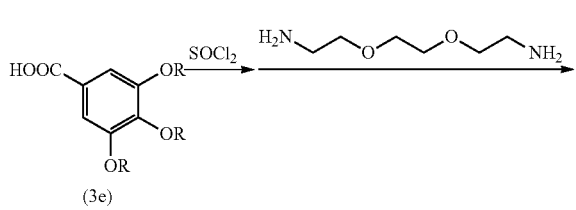

Compound (49)

R = OCCH$_2$CH$_2$COOCH$_2$CH$_2$C$_6$F$_{13}$

Compound (49) was obtained by using the same procedures used in Example 4, except that the diol (3d) used in (24-2) for the synthesis of compound (24) was replaced with 1,2-bis(2-aminoethoxy)ethane.

$^1$H NMR (300 MHz, CDCl$_3$) δ 2.4-2.6 (m, 12H), 2.7-2.8 (m, 12H), 2.8-3.0 (m, 12H), 3.5-3.7 (m, 12H), 4.3-4.5 (m, 12H), 6.9-7.0 (m, 2H), 7.6 (s, 4H)

Example 8

Compound (51) was synthesized by using the following route.

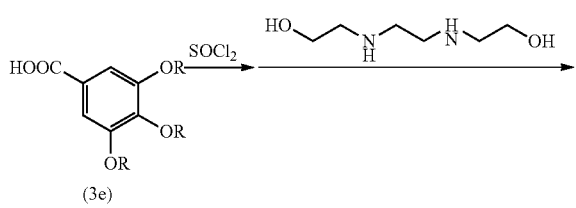

Compound (51)

R = OCCH$_2$CH$_2$COOCH$_2$CH$_2$C$_6$F$_{13}$

Compound (51) was obtained by using the same procedures used in Example 4, except that the diol (3d) used in (24-2) for the synthesis of compound (24) was replaced with 3,6-diazaoctane-1,8-diol.

$^1$H NMR (300 MHz, CDCl$_3$) δ 2.4-2.6 (m, 12H), 2.7-2.8 (m, 12H), 2.8-3.0 (m, 12H), 3.2-3.3 (m, 4H), 3.5-3.6 (m, 4H), 3.8-4.0 (m, 4H), 4.3-4.5 (m, 12H), 7.8 (s, 4H)

Example 9

Compound (52) was synthesized by using the following route.

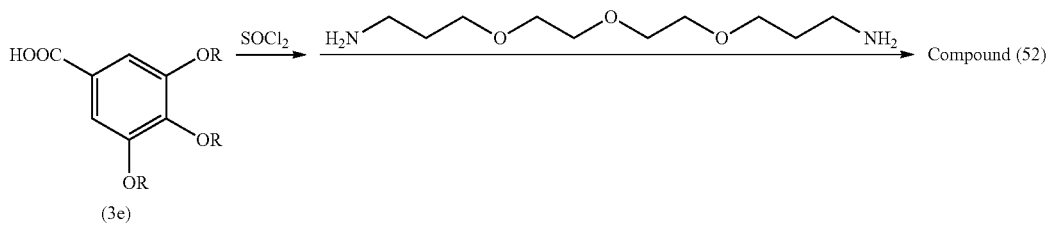

Compound (52) was obtained by using the same procedures used in Example 4, except that the diol (3d) used in (24-2) for the synthesis of compound (24) was replaced with diethylene glycolbis(3-aminopropyl)ether.

$^1$H NMR (300 MHz, CDCl$_3$) δ 1.8-1.9 (m, 4H), 2.4-2.6 (m, 12H), 2.7-2.8 (m, 12H), 2.8-3.0 (m, 12H), 3.5-3.7 (m, 16H), 4.3-4.4 (m, 12H), 7.6 (s, 4H)

Example 10

Compound (53) was synthesized by using the following route.

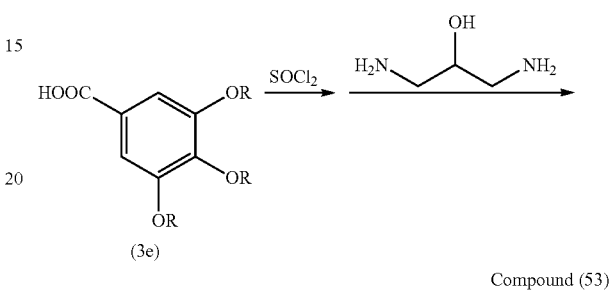

Compound (53)

R = OCCH$_2$CH$_2$COOCH$_2$CH$_2$C$_6$F$_{13}$

Compound (53) was obtained by using the same procedures used in Example 4, except that the diol (3d) used in (24-2) for the synthesis of compound (24) was replaced with 1,3-diamino-2-propanol.

$^1$H NMR (300 MHz, CDCl$_3$) δ 2.4-2.6 (m, 12H), 2.7-2.8 (m, 12H), 2.8-3.0 (m, 12H), 3.4-3.5 (m, 4H), 3.8-3.9 (m, 1H), 3.9-4.0 (m, 1H), 4.3-4.5 (m, 1H), 7.8 (s, 4H)

Examples 11 to 22, and Comparative Example 1

Optically anisotropic films were formed with the liquid crystal alignment promoting agents shown in Table 1, and the film of each Example and Comparative Example was evaluated.

Coating Liquid Preparation

First, a coating liquid of the composition below was prepared. The coating liquid was prepared to make the concentration of the liquid crystal alignment promoting agent 0.10 parts by mass or 0.20 parts by mass with respect to the rod-like liquid crystal compound.

Rod-like liquid crystal compound 1: 100 parts by mass
Chiral agent (A): 5.0 parts by mass
IRGACURE 819 (Ciba Japan): 3 parts by mass
Liquid crystal alignment promoting agents shown in Table 1: as above
Solvents shown in Table 1: amounts that make the solute concentration 25 mass %

Rod-Like Liquid Crystal Compound 1
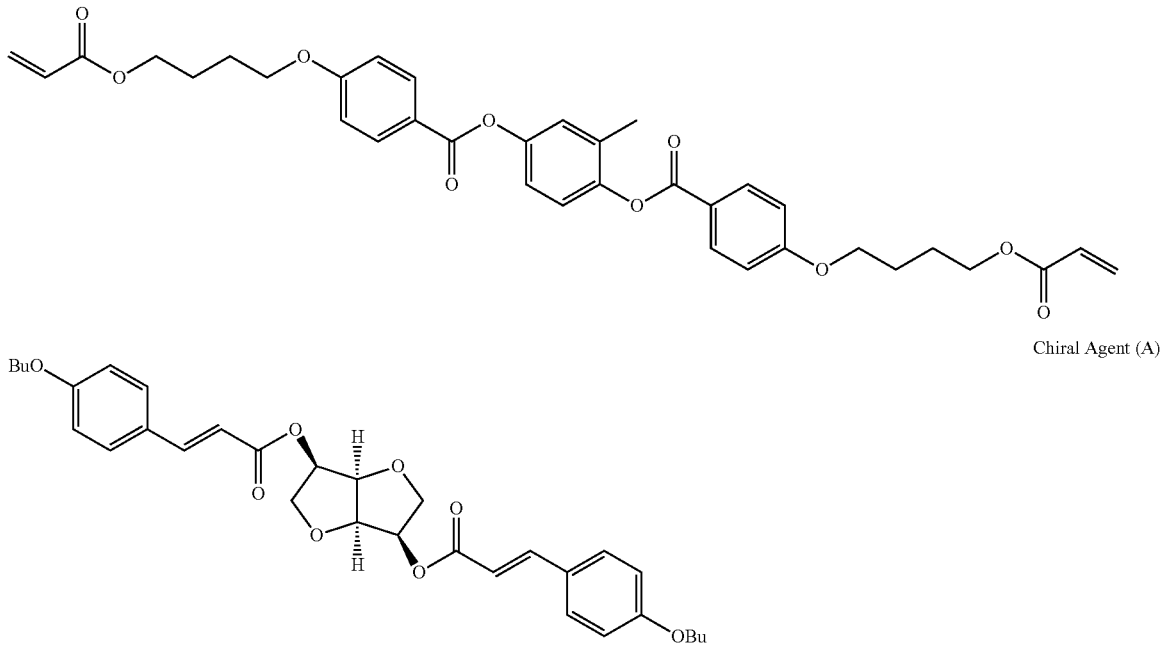
Chiral Agent (A)
Liquid Crystal Alignment Promoting Agents of Formula (1)
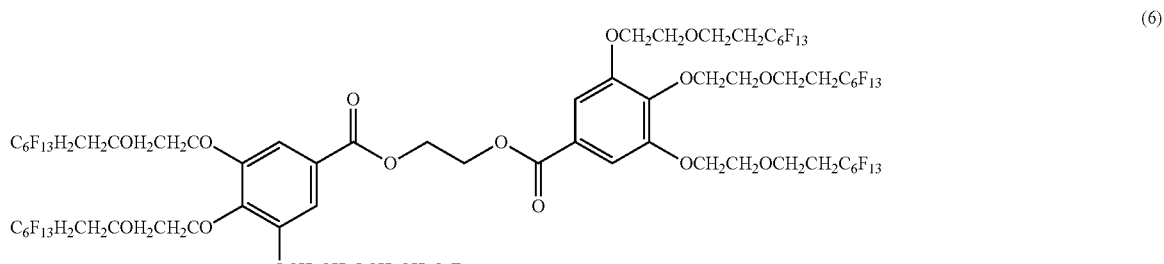
(6)
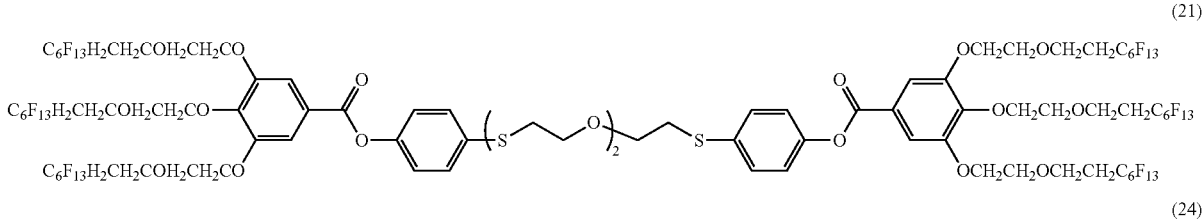
(21)
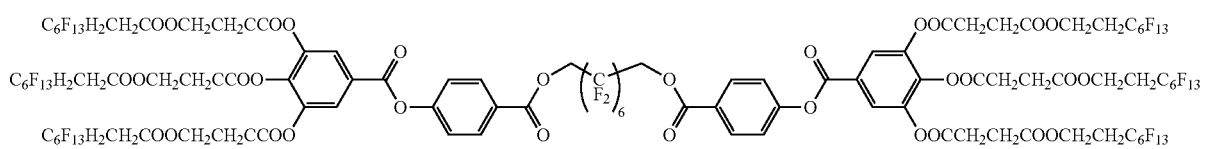
(24)
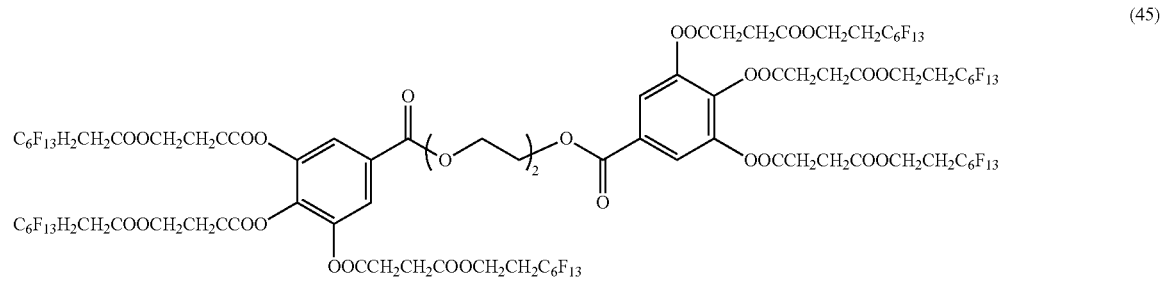
(45)

-continued
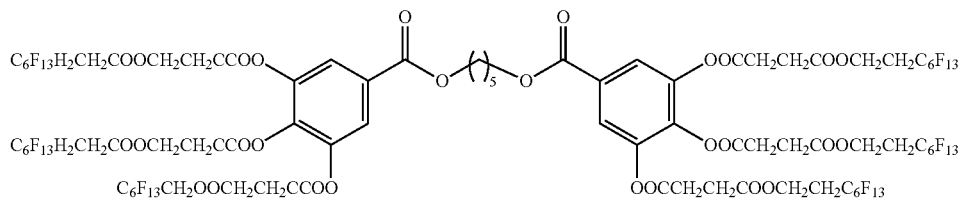
(46)
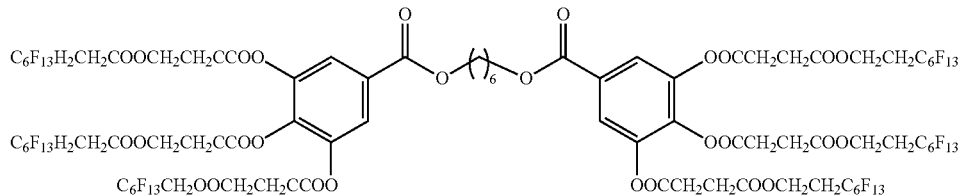
(47)
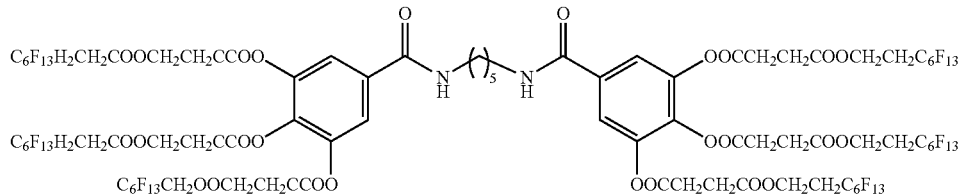
(48)
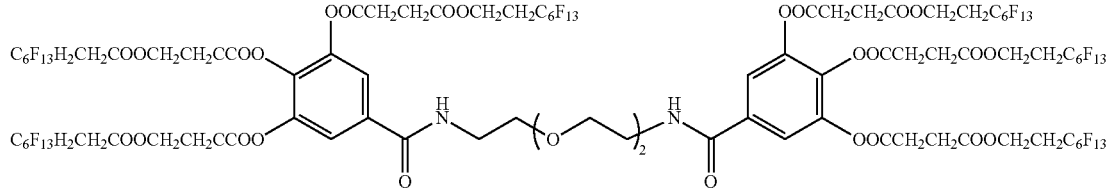
(49)
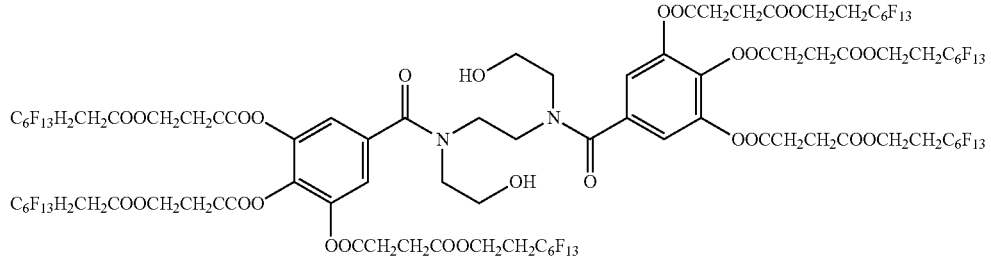
(51)
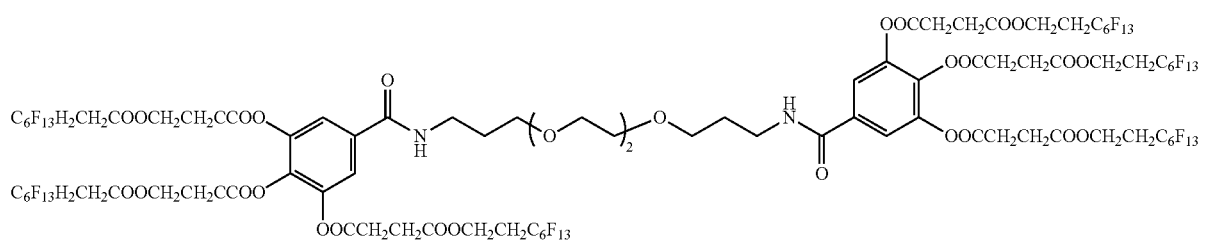
(52)
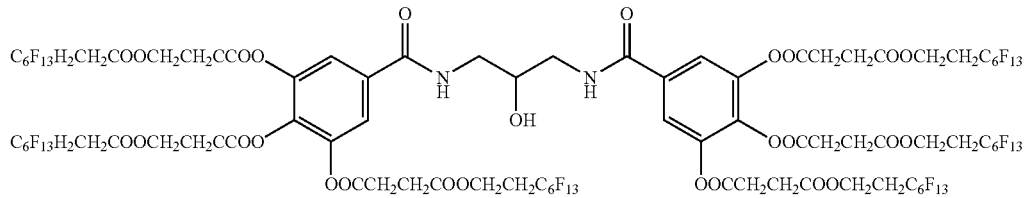
(53)
[Compound (30) of JP-A-2002-129162]

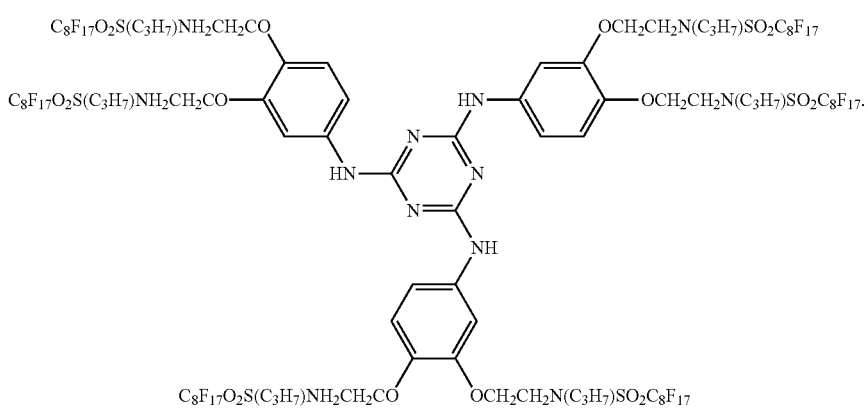

Compound (A)

Preparation of Optically Anisotropic Film

Fifty microliters of the coating liquid prepared was taken into a micropipetter, dropped onto an alignment film-attached glass (SE-130), and spin coated at a 2,000 rpm rotation speed. The sample was heated at 85° C. for 2 min, allowed to cool for 1 min, and irradiated with ultraviolet light in a nitrogen atmosphere (ultraviolet intensity: 500 mJ/m$^2$) to form an optically anisotropic film of each Example and Comparative Example. The optically anisotropic films of Examples and Comparative Example had a thickness of about 5 μm.

The film of Example 11 was taken as a representative film, and the transmission spectrum of the film was measured with a spectrophotometer UV-3100PC(SHIMADZU). The result is shown in FIG. 1. As shown in FIG. 1, the film produced in Example 11 was a selective reflecting film that had a center wavelength in the near-infrared region near 900 nm, and had optical anisotropy.

Dissolution and Alignment Promotion Test

The orientation of the film of each Example and Comparative Example was evaluated by visual inspection and haze. Haze was measured with a haze mater NDH2000 (Nippon Denshoku).

In the alignment test, the alignment promoting effect was evaluated using the haze values of the films containing the liquid crystal alignment promoting agent in 0.10 mass % and 0.20 mass %. The films were evaluated according to the following criteria.

Samples with higher ratings have greater alignment promoting effects.

Good: Less than 1.00
Poor: 1.00 or more

The results are presented in Table 1 below.

TABLE 1

| | Liquid crystal alignment promoting agent | Solvent | Dissolution and alignment promotion test | |
|---|---|---|---|---|
| | | | Concentration 0.10 mass % | Concentration 0.20 mass % |
| Ex. 11 | Compound (1) | Chloroform | Good | Good |
| Ex. 12 | Compound (6) | Chloroform | Good | Good |
| Ex. 13 | Compound (21) | Chloroform | Good | Good |
| Ex. 14 | Compound (24) | Chloroform | Good | Good |
| Ex. 15 | Compound (45) | Chloroform | Good | Good |
| Ex. 16 | Compound (46) | Chloroform | Good | Good |
| Ex. 17 | Compound (47) | Chloroform | Good | Good |
| Ex. 18 | Compound (48) | Chloroform | Good | Good |
| Ex. 19 | Compound (49) | Chloroform | Good | Good |
| Ex. 20 | Compound (51) | Chloroform | Good | Good |
| Ex. 21 | Compound (52) | Chloroform | Good | Good |
| Ex. 22 | Compound (53) | Chloroform | Good | Good |
| Com. Ex. 1 | Compound (A) | Chloroform | Good | Poor |

As shown in Table 1, it was confirmed that the compounds of the present invention had greater haze lowering effects, and higher solubility for the solvent even at increased concentrations. Though not being bound to any theory, such haze reductions are believed to be due to the large liquid crystal alignment effect of the compounds of the present invention providing desirable liquid crystal alignment also on the air interface side. Specifically, it can be said that the compounds of the present invention are haze-lowering agents and liquid crystal alignment promoting agents.

The tendency remained the same also in liquid crystal haze lowering tests conducted with films produced in the same manner as in Examples 11 to 22 except that the solvent was changed to methyl ethyl ketone, and that the solute concentration was changed to 33%. The result confirmed that the compounds of the present invention were applicable to a wide range of coating solvents, and were highly competent.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/055720 filed Mar. 1, 2013; and Japanese Patent Application No. 2012-050097 filed Mar. 7, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. A liquid crystal composition comprising a compound represented by the following formula (1), and a liquid crystal molecule:

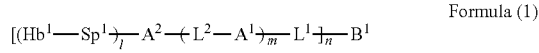

Formula (1)

wherein:
B$^1$ represents an n-valent chain linking group of 1 to 40 carbon atoms, wherein a methylene group in the n-valent chain linking group may be substituted with —O—, —S—, —CO—, —COO—, —OCO—, —COS—, —SCO—, —NR$^2$CO—, —CONR$^2$—, —NR$^2$CONR$^2$—, —NR$^2$—, —CR$^2$=CR$^2$—, —C≡C—, or —CR$^2$R$^2$— in which R$^2$ each independently represents a hydrogen atom, or an alkyl group of 1 to 10 carbon atoms, and a hydrogen atom in the n-valent chain linking group may be substituted with a halogen atom, —COOH, —SO$_3$H, —SH, —NH$_3$, or —OH, provided that any two consecutive methylene groups are not both substituted and B$^1$ does not contain a cyclic structure and wherein the chain linking group contains at least one —CR$^{101}$R$^{102}$—, and R$^{101}$ and R$^{102}$ each independently represent a hydrogen atom, a halogen atom, —COOH, —SO$_3$H, —SH, —NH$_3$, or —OH, and not containing a cyclic structure, L$^1$ and L$^2$ each independently represent a single bond, —O—, —S—, —CO—, —COO—, —OCO—, —COS—, —SCO—, —C(=S)O—, —NR$^0$CO—, or —CONR$^0$— wherein R$^0$ represents a hydrogen atom or an alkyl group of 1 to 6 carbon atoms, A$^1$ represents a divalent aromatic hydrocarbon group or a divalent heterocyclic group, A$^2$ represents an (l+1)-valent aromatic hydrocarbon group, Sp$^1$ represents a single bond, or an alkylene group of 1 to 10 carbon atoms wherein a methylene group in the alkylene group may be substituted with —O—, —S—, —CO—, —COO—, —OCO—, —COS—, —SCO—, —NR$^1$CO—, or —CONR$^1$— in which R$^1$ represents a hydrogen atom, or an alkyl group of 1 to 6 carbon atoms, provided that any two consecutive methylene groups are not both substituted, and wherein a hydrogen atom of the alkylene may be substituted with a halogen atom or a hydroxyl group, Hb$^1$ represents a fluorine-substituted alkyl group of 4 to 30 carbon atoms, n represents an integer of 2, m represents an integer of 0 to 2, l represents 2 or 3, and L$^1$, L$^2$, A$^1$, A$^2$, Sp$^1$, Hb$^1$, m, and l occurring more than once in formula (1) may be the same or different.

2. The liquid crystal composition according to claim 1, wherein B$^1$ in the formula (1) contains at least one unsubstituted methylene group.

3. The liquid crystal composition according to claim 1, wherein, in the formula (1),
B$^1$ represents an alkylene group of 1 to 40 carbon atoms, wherein a methylene group in the alkylene group may be substituted with —O—, —S—, —CO—, —COO—, —OCO—, —COS—, —SCO—, —NR$^2$CO—, —CONR$^2$—, —NR$^2$CONR$^2$—, —NR$^2$—, —CR$^2$=CR$^2$—, —C≡C—, or —CR$^2$R$^2$— in which R$^2$ each independently represents a hydrogen atom, or an alkyl group of 1 to 10 carbon atoms, and a hydrogen atom in the alkylene group may be substituted with a halogen atom, —COOH, —SO$_3$H, —SH, —NH$_3$, or —OH, provided that any two consecutive methylene groups are not both substituted and
B$^1$ does not contain a cyclic structure.

4. The liquid crystal composition according to claim 1, wherein, in the formula (1),
B$^1$ represents alkylene of 1 to 40 carbon atoms, wherein a methylene group in the alkylene group may be substituted with —O—, —S—, —CO—, —COO—, —OCO—, —COS—, —SCO—, —NR$^5$CO—, —CONR$^5$—, or —NR$^5$CONR$^5$— in which R$^5$ each independently represents a hydrogen atom, or an alkyl group of 1 to 6 carbon atoms, and a hydrogen atom in the alkylene may be substituted with a halogen atom, provided that any two consecutive methylene groups are not both substituted, and
B$^1$ does not contain a cyclic structure.

5. The liquid crystal composition according to claim 1, wherein, in the formula (1),
B$^1$ represents alkylene of 1 to 40 carbon atoms, wherein a methylene group in the alkylene group may be substituted with —O—, —S—, —NR$^6$—, or —NR$^6$CONR$^6$— in which R$^6$ each independently represents a hydrogen atom, or an alkyl group of 1 to 6 carbon atoms, and a hydrogen atoms in the alkylene group may be substituted with a halogen atom, provided that any two consecutive methylene groups are not both substituted.

6. The liquid crystal composition according to claim 1, wherein the compound represented by the formula (1) is a compound represented by the following formula (2):

Formula (2)

wherein B$^{11}$ represents alkylene of 1 to 40 carbon atoms wherein a methylene group in the alkylene may be substituted with —O—, —S—, —CO—, —COO—, —OCO—, —COS—, —SCO—, —NR$^{12}$CO—, —CONR$^{12}$—, —NR$^{12}$CONR$^{12}$—, —NR$^{12}$—, —CR$^{12}$=CR$^{12}$, —C≡C—, or —CR$^{12}$R$^{12}$— in which R$^{12}$ each independently represents a hydrogen atom, or an alkyl group of 1 to 10 carbon atoms, provided that any two consecutive methylene groups are not both substituted, and wherein a hydrogen atom in the alkylene group may be substituted with a halogen atom, provided that that the alkylene group contains at least one unsubstituted methylene group, and wherein B$^{11}$ does not contain a cyclic structure, L$^{11}$ represents —COO—, —COS—, or —CONR$^{10}$—, L$^{12}$ represents a single bond, —O—, —S—, —CO—, —COO—, —OCO—, —COS—, —SCO—, —NR¹⁰CO—, or —CONR¹⁰— in which R¹⁰ each independently represents a hydrogen atom, or an alkyl group of 1 to 6 carbon atoms, A¹¹ represents a divalent aromatic hydrocarbon group or a divalent heterocyclic group, A¹² represents an (s+1)-valent aromatic hydrocarbon group, Sp¹¹ represents a single bond, or an alkylene group of 1 to 10 carbon atoms wherein a methylene group in the alkylene group may be substituted with —O—, —S—, —CO—, —COO—, —OCO—, —COS—, —SCO—, —NR¹¹CO—, or —CONR¹¹— in which R¹¹ represents a hydrogen atom, or an alkyl group of 1 to 6 carbon atoms, and a hydrogen atom in the alkylene group may be substituted with a halogen atom, Hb¹¹ represents a fluorine-substituted alkyl group of 4 to 30 carbon atoms, t represents an integer of 0 to 2, s represents 2 or 3, and L¹¹, L¹², A¹¹, A¹², Sp¹¹, Hb¹¹, s and t occurring more than once in formula (2) each independently may be the same or different.

7. The liquid crystal composition according to claim 6, wherein s in the formula (2) is 3.

8. The liquid crystal composition according to claim 6, wherein, in the formula (2), t represents 0 or 1, and L¹¹ and L¹² are both —COO—.

9. The liquid crystal composition according to claim 1, wherein the liquid crystal molecule is a polymerizable rod-like liquid crystal molecule.

10. The liquid crystal composition according to claim 1, wherein the liquid crystal composition further contains at least one chiral compound.

11. A polymer material which is a polymerized material of a liquid crystal composition comprising a compound represented by the following formula (1) and a liquid crystal molecule:

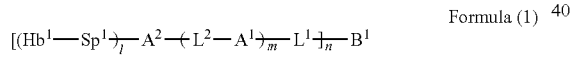

Formula (1)

wherein:
B¹ represents an n-valent chain linking group of 1 to 40 carbon atoms wherein the chain linking group contains at least one —CR¹⁰¹R¹⁰²—, and R¹⁰¹ and R¹⁰² each independently represent a hydrogen atom, a halogen atom, —COOH, —SO₃H, —SH, —NH₃, or —OH, and not containing a cyclic structure, L¹ and L² each independently represent a single bond, —O—, —S—, —CO—, —COO—, —OCO—, —COS—, —SCO—, —C(=S)O—, —NR⁰CO—, or —CONR⁰— wherein R⁰ represents a hydrogen atom or an alkyl group of 1 to 6 carbon atoms, A¹ represents a divalent aromatic hydrocarbon group or a divalent heterocyclic group, A² represents an (l+1)-valent aromatic hydrocarbon group, Sp¹ represents a single bond, or an alkylene group of 1 to 10 carbon atoms wherein a methylene group in the alkylene group may be substituted with —O—, —S—, —CO—, —COO—, —OCO—, —COS—, —SCO—, —NR¹CO—, or —CONR¹— in which R¹ represents a hydrogen atom, or an alkyl group of 1 to 6 carbon atoms, provided that any two consecutive methylene groups are not both substituted, and wherein a hydrogen atom of the alkylene may be substituted with a halogen atom or a hydroxyl group, Hb¹ represents a fluorine-substituted alkyl group of 4 to 30 carbon atoms, n represents an integer of 2 to 6, m represents an integer of 0 to 2, l represents 2 or 3, and L¹, L², A¹, A², Sp¹, Hb¹, m, and l occurring more than once in formula (1) may be the same or different.

12. A film that contains at least one polymer material which is a polymerized material of a liquid crystal composition comprising a compound represented by the following formula (1) and a liquid crystal molecule:

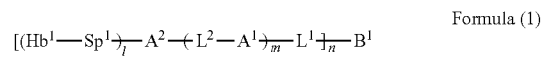

Formula (1)

wherein:
B¹ represents an n-valent chain linking group of 1 to 40 carbon atoms wherein the chain linking group contains at least one —CR¹⁰¹R¹⁰²—, and R¹⁰¹ and R¹⁰² each independently represent a hydrogen atom, a halogen atom, —COOH, —SO₃H, —SH, —NH₃, or —OH, and not containing a cyclic structure, L¹ and L² each independently represent a single bond, —O—, —S—, —CO—, —COO—, —OCO—, —COS—, —SCO—, —C(=S)O—, —NR⁰CO—, or —CONR⁰— wherein R⁰ represents a hydrogen atom or an alkyl group of 1 to 6 carbon atoms, A¹ represents a divalent aromatic hydrocarbon group or a divalent heterocyclic group, A² represents an (l+1)-valent aromatic hydrocarbon group, Sp¹ represents a single bond, or an alkylene group of 1 to 10 carbon atoms wherein a methylene group in the alkylene group may be substituted with —O—, —S—, —CO—, —COO—, —OCO—, —COS—, —SCO—, —NR¹CO—, or —CONR¹— in which R¹ represents a hydrogen atom, or an alkyl group of 1 to 6 carbon atoms, provided that any two consecutive methylene groups are not both substituted, and wherein a hydrogen atom of the alkylene may be substituted with a halogen atom or a hydroxyl group, Hb¹ represents a fluorine-substituted alkyl group of 4 to 30 carbon atoms, n represents an integer of 2 to 6, m represents an integer of 0 to 2, l represents 2 or 3, and L¹, L², A¹, A², Sp¹, Hb¹, m, and l occurring more than once in formula (1) may be the same or different.

13. A film with a fixed cholesteric liquid crystal phase of the liquid crystal composition comprising a compound represented by the following formula (1) and a liquid crystal molecule:

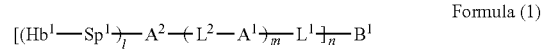

Formula (1)

wherein:
B¹ represents an n-valent chain linking group of 1 to 40 carbon atoms wherein the chain linking group contains at least one —CR¹⁰¹R¹⁰²—, and R¹⁰¹ and R¹⁰² each independently represent a hydrogen atom, a halogen atom, —COOH, —SO$_3$H, —SH, —NH$_3$, or —OH, and not containing a cyclic structure, L$^1$ and L$^2$ each independently represent a single bond, —O—, —S—, —CO—, —COO—, —OCO—, —COS—, —SCO—, —C(=S)O—, —NR$^0$CO—, or —CONR$^0$— wherein R$^0$ represents a hydrogen atom or an alkyl group of 1 to 6 carbon atoms, A$^1$ represents a divalent aromatic hydrocarbon group or a divalent heterocyclic group, A$^2$ represents an (l+1)-valent aromatic hydrocarbon group, Sp$^1$ represents a single bond, or an alkylene group of 1 to 10 carbon atoms wherein a methylene group in the alkylene group may be substituted with —O—, —S—, —CO—, —COO—, —OCO—, —COS—, —SCO—, —NR$^1$CO—, or —CONR$^1$— in which R$^1$ represents a hydrogen atom, or an alkyl group of 1 to 6 carbon atoms, provided that any two consecutive methylene groups are not both substituted, and wherein a hydrogen atom of the alkylene may be substituted with a halogen atom or a hydroxyl group, Hb$^1$ represents a fluorine-substituted alkyl group of 4 to 30 carbon atoms, n represents an integer of 2 to 6, m represents an integer of 0 to 2, l represents 2 or 3, and L$^1$, L$^2$, A$^1$, A$^2$, Sp$^1$, Hb$^1$, m, and l occurring more than once in formula (1) may be the same or different.

14. The film according to claim 12, wherein the film has optical anisotropy.

15. The film according to claim 12, wherein the film has a selective reflection characteristic.

16. The film according to claim 15, wherein the film has a selective reflection characteristic in an infrared wavelength region.

* * * * *